US011576845B2

(12) United States Patent
Parthasarathy et al.

(10) Patent No.: US 11,576,845 B2
(45) Date of Patent: Feb. 14, 2023

(54) METHODS OF REMOVING SPORES COMPRISING ALCOHOL, ACRYLATE COPOLYMER PARTICLES, AND A CATIONIC COATED ARTICLE

(71) Applicant: 3M INNOVATIVE PROPERTIES COMPANY, Saint Paul, MN (US)

(72) Inventors: Ranjani V. Parthasarathy, Woodbury, MN (US); Ramesh C. Kumar, Woodbury, MN (US); Matthew T. Scholz, Woodbury, MN (US); Steven P. Swanson, Blaine, MN (US); Andrew W. Vail, Woodbury, MN (US); Jerald K. Rasmussen, Woodville, WI (US); George W. Griesgraber, Eagan, MN (US); Catherine D. Heapy, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 150 days.

(21) Appl. No.: 16/475,260

(22) PCT Filed: Jan. 2, 2018

(86) PCT No.: PCT/US2018/012033
§ 371 (c)(1),
(2) Date: Jul. 1, 2019

(87) PCT Pub. No.: WO2018/128965
PCT Pub. Date: Jul. 12, 2018

(65) Prior Publication Data
US 2019/0336409 A1 Nov. 7, 2019

Related U.S. Application Data

(60) Provisional application No. 62/442,046, filed on Jan. 4, 2017.

(51) Int. Cl.
| | | |
|---|---|---|
| *C11D 7/22* | (2006.01) | |
| *A61K 8/02* | (2006.01) | |
| *A01N 25/10* | (2006.01) | |
| *A01N 31/02* | (2006.01) | |
| *A01N 47/44* | (2006.01) | |
| *A61K 8/34* | (2006.01) | |
| *A61K 8/81* | (2006.01) | |
| *A61K 8/84* | (2006.01) | |
| *A61L 2/00* | (2006.01) | |
| *A61Q 17/00* | (2006.01) | |

(52) U.S. Cl.
CPC ............ *A61K 8/0208* (2013.01); *A01N 25/10* (2013.01); *A01N 31/02* (2013.01); *A01N 47/44* (2013.01); *A61K 8/34* (2013.01); *A61K 8/8152* (2013.01); *A61K 8/84* (2013.01); *A61L 2/0088* (2013.01); *A61Q 17/005* (2013.01); *A61K 2800/884* (2013.01); *A61L 2202/17* (2013.01)

(58) Field of Classification Search
CPC ...................................................... C11D 3/201
See application file for complete search history.

(56) References Cited

U.S. PATENT DOCUMENTS

| | | | |
|---|---|---|---|
| 4,384,097 A | | 5/1983 | Wingler et al. |
| 5,480,633 A | * | 1/1996 | Simion ................. A61Q 19/00 514/846 |
| 5,712,027 A | | 1/1998 | Ali |
| 5,951,993 A | | 9/1999 | Scholz |
| 6,383,505 B1 | | 5/2002 | Kaiser |
| 6,484,735 B1 | | 11/2002 | Gordon |

(Continued)

FOREIGN PATENT DOCUMENTS

| | | |
|---|---|---|
| CA | 2111932 | 6/1994 |
| CA | 2246913 | 3/1999 |

(Continued)

OTHER PUBLICATIONS

Supplementary European Search Report for EP 18736460 dated May 20, 2020.
Katritzky, "Comprehensive Organic Functional Group Transformation", 1995, vol. 6, pp. 640.
Rasmussen, "Crosslinked, Hydrophilic, Azlactone-Functional Polymeric Beads: A Two-Step Approach", Reactive Polymers, 1991/1992, vol. 16, pp. 199-212.
Rose, "Bisdiguanides having Antibacterial Activity", Journal of Chemical Society, 1956, pp. 4422-4425.

(Continued)

*Primary Examiner* — Charles I Boyer

(57) ABSTRACT

Disclosed herein are methods that include contacting a skin surface with a first liquid composition; and then contacting in the skin surface with a cationic coated article loaded with a second liquid composition, while at least some portion of the first liquid composition remains on the skin surface, wherein one or both of the first liquid composition or the second liquid composition includes acrylate copolymer particles dispersed therein, the acrylate copolymer particles including the reaction product of a reaction mixture, the reaction mixture including monomers, the monomers including from about 5 wt % to about 50 wt % of at least one high Tg monomer where the wt % of the high Tg monomer is with respect to the total weight of the monomers in the reaction mixture; and from about 20 wt % to about 80 wt % of at least one low Tg monomer where the wt % of the low Tg monomer is with respect to the total weight of the monomers in the reaction mixture, wherein the particles have a number average diameter of at least about 100 nm and wherein at least one and only one of the first or the second composition comprises greater than or equal to 60 wt % of at least one alcohol.

15 Claims, 1 Drawing Sheet

(56) References Cited

U.S. PATENT DOCUMENTS

Figure 1A:
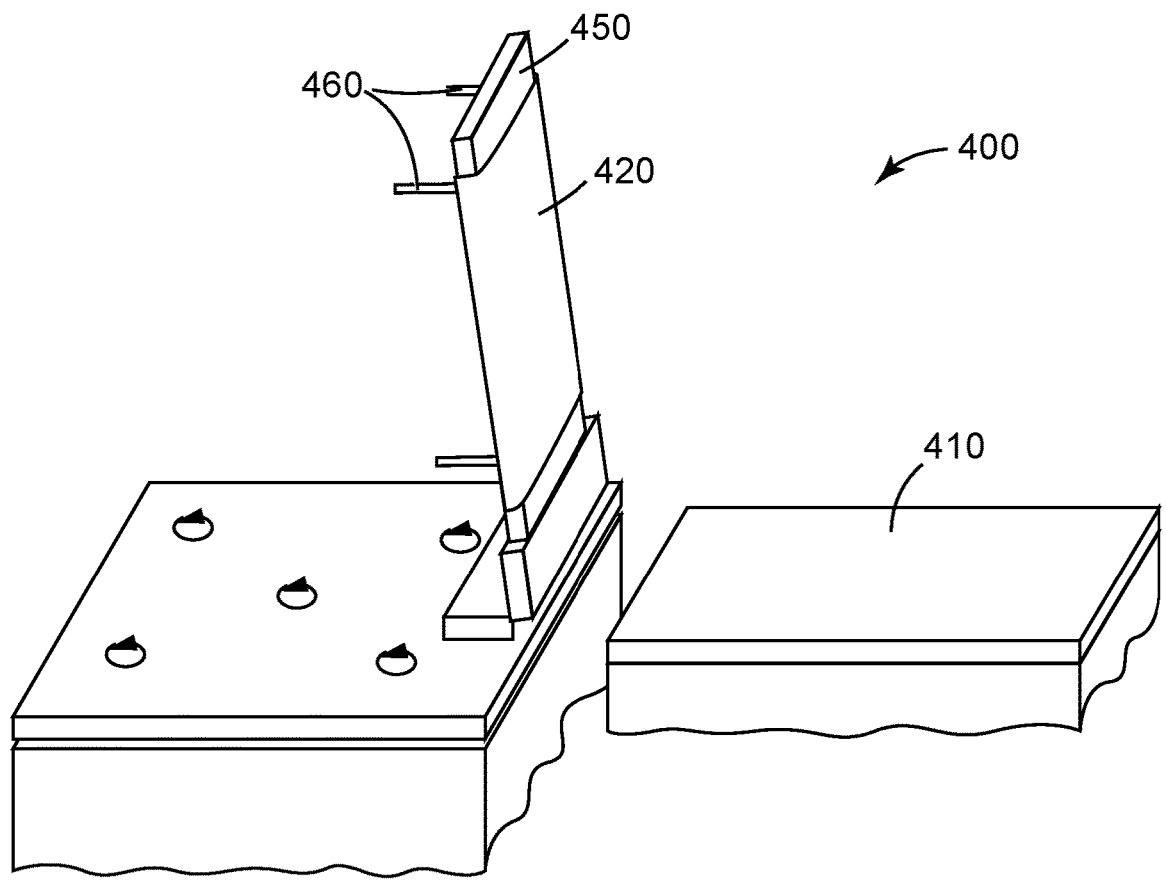

| | | |
|---|---|---|
| 7,101,621 B2 | 9/2006 | Haddad |
| 7,576,047 B2 | 8/2009 | Kilkenny |
| 8,062,649 B2 | 11/2011 | Asmus |
| 8,377,672 B2 | 2/2013 | Rasmussen |
| 8,551,894 B2 | 10/2013 | Seshadri et al. |
| 2005/0261159 A1 | 11/2005 | Parris |
| 2006/0035807 A1* | 2/2006 | Kasturi .............. A61K 8/44 |
| | | 510/475 |
| 2006/0141017 A1 | 6/2006 | Kling |
| 2007/0054827 A1 | 3/2007 | Cheung |
| 2007/0129641 A1 | 6/2007 | Sweeney |
| 2007/0184016 A1 | 8/2007 | Macinga |
| 2007/0244027 A1 | 10/2007 | Sivik |
| 2008/0044479 A1 | 2/2008 | Stack |
| 2008/0102053 A1 | 5/2008 | Childers |
| 2008/0152614 A1 | 6/2008 | Dunshee |
| 2009/0301519 A1 | 12/2009 | Aubay |
| 2010/0040700 A1 | 2/2010 | Cruz |
| 2010/0075560 A1 | 3/2010 | Seshadri |
| 2010/0136069 A1 | 6/2010 | Deckner |
| 2010/0282409 A1* | 11/2010 | Hobbs .............. A61P 31/10 |
| | | 156/327 |
| 2011/0152925 A1* | 6/2011 | Schorr .............. A61P 17/00 |
| | | 606/214 |
| 2012/0087963 A1 | 4/2012 | Evans et al. |
| 2015/0136698 A1* | 5/2015 | Bothof .............. C08F 283/04 |
| | | 210/651 |
| 2016/0115430 A1* | 4/2016 | Swanson .............. C11D 17/049 |
| | | 134/6 |
| 2017/0196780 A1* | 7/2017 | Mizuno .............. A61K 8/345 |

FOREIGN PATENT DOCUMENTS

| | | |
|---|---|---|
| CA | 2621986 | 8/2008 |
| DE | 102004058143 | 5/2006 |
| EP | 0971997 | 1/2000 |
| KR | 2003-0085436 | 11/2003 |
| WO | WO 2000-30599 | 6/2000 |
| WO | WO 2001-41727 | 6/2001 |
| WO | WO 2003-066001 | 8/2003 |
| WO | WO 2006-013315 | 2/2006 |
| WO | WO 2006-084251 | 8/2006 |
| WO | WO 2008-003632 | 1/2008 |
| WO | WO 2009-112843 | 9/2009 |
| WO | WO 2011-103106 | 8/2011 |
| WO | WO 2011-109151 | 9/2011 |
| WO | 2012107847 A2 | 8/2012 |
| WO | WO 2012/107847 | 8/2012 |
| WO | WO 2014-204763 | 12/2014 |
| WO | WO 2014-209798 | 12/2014 |
| WO | WO 2017-003923 | 1/2017 |
| WO | WO 2018-128966 | 7/2018 |

OTHER PUBLICATIONS

Wente, "Superfine Thermoplastic Fibers", Industrial and Engineering Chemistry, 1956, vol. 48, No. 8, pp. 1342-1346.

Wente, "Manufacture of Superfine Organic Fibers", Navel Research Report No. 4364, 1954, 19 Pages.

International Search Report for PCT International Application No. PCT/US2018/012033, dated Mar. 6, 2018, 3pgs.

* cited by examiner

METHODS OF REMOVING SPORES COMPRISING ALCOHOL, ACRYLATE COPOLYMER PARTICLES, AND A CATIONIC COATED ARTICLE

CROSS REFERENCE TO RELATED APPLICATIONS

This application is a national stage filing under 35 U.S.C. 371 of PCT/US2018/012033, filed Jan. 2, 2018, which claims the benefit of U.S. Provisional Application No. 62/442,046, filed Jan. 4, 2017, the disclosures of which are incorporated by reference in their entirety herein.

FIELD

The present disclosure relates to methods of removing spores from surfaces.

BACKGROUND

There is a great deal of interest and urgency in preventing the spread of *C. difficile*, particularly in medical settings such as hospitals. Patients in a hospital setting often times develop *C. difficile* infections during or shortly after a course of antibiotics. While it is relatively easy to kill the vegetative form of *C. difficile*, the spore form of *C. difficile*, can be very difficult to kill. New technologies are therefore needed to address the problem of preventing the spread of *C. difficile*, between patients, health care workers, and the environment.

SUMMARY

Disclosed herein are methods that include contacting a skin surface with a first liquid composition; and then contacting the skin surface with a cationic coated article loaded with a second liquid composition, while at least some portion of the first liquid composition remains on the skin surface, wherein one or both of the first liquid composition or the second liquid composition includes acrylate copolymer particles dispersed therein, the acrylate copolymer particles including the reaction product of a reaction mixture, the reaction mixture including monomers, the monomers including from about 5 wt % to about 50 wt % of at least one high Tg monomer where the wt % of the high Tg monomer is with respect to the total weight of the monomers in the reaction mixture; and from about 20 wt % to about 80 wt % of at least one low Tg monomer where the wt % of the low Tg monomer is with respect to the total weight of the monomers in the reaction mixture, wherein the particles have a number average diameter of at least about 100 nm and wherein at least one and only one of the first or the second composition comprises greater than or equal to 60 wt % of at least one alcohol.

The above summary of the present disclosure is not intended to describe each disclosed embodiment or every implementation of the present disclosure. The description that follows more particularly exemplifies illustrative embodiments. In several places throughout the application, guidance is provided through lists of examples; examples can be used in various combinations. In each instance, the recited list serves only as a representative group and should not be interpreted as an exclusive list.

BRIEF DESCRIPTION OF THE DRAWINGS

FIGS. 1A and 1B are schematic views of a mechanical wiping device used in testing wipes.

DETAILED DESCRIPTION

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, "top" and "bottom" (or other terms like "upper" and "lower") are utilized strictly for relative descriptions and do not imply any overall orientation of the article in which the described element is located.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects is present. For example, a "second" substrate is merely intended to differentiate from another substrate (such as a "first" substrate). Use of "first," "second," etc. in the description above and the claims that follow is also not necessarily intended to indicate that one comes earlier in time than the other.

As used herein the term "spore" refers to microbial spores.

As used herein, "polymer" is inclusive of a homopolymer, copolymer, terpolymer, and the like.

As used herein, "(meth)acrylic" is inclusive of both methacrylic and acrylic. Likewise, the term "(meth)acrylamide" refers to both methacrylamide and acrylamide and the term "(meth)acrylate refers to both methacrylate and acrylate.

As used herein, the term "bound" or "binding" in reference to the cationic coating (e.g., the guanidinyl-containing polymer in the cationic coating) being bound to the substrate or binding the cationic coating to the substrate means that the cationic coating cannot be removed without destroying the substrate. The cationic coating can be chemically attached to the substrate or can be crosslinked around the fibers of the substrate such that the coating cannot be removed by peeling, dissolving in water or an organic solvent.

As used herein, "alkyl" refers to a monovalent radical of an alkane and includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like.

As used herein, "alkylene" refers to a divalent radical of an alkane and includes straight-chained, branched, and cyclic alkylene groups and includes both unsubstituted and substituted alkylene groups. Unless otherwise indicated, the alkyl groups typically contain from 1 to 20 carbon atoms. Examples of "alkylene" as used herein include, but are not limited to, methylene, ethylene, n-propylene, n-butylene, n-pentylene, isobutylene, t-butylene, isopropylene, n-octylene, n-heptylene, ethylhexylene, cyclopentylene, cyclohexylene, cycloheptylene, adamantylene, and norbornylene, and the like.

As used herein, "aryl" is a monovalent radical of an aromatic group containing 5-12 ring atoms and can contain optional fused rings, which may be saturated, unsaturated, or aromatic. Examples of an aryl groups that are carbocyclic include phenyl, naphthyl, biphenyl, phenanthryl, and anthracyl. The term "heteroaryl" refers to an aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. The term "(hetero)aryl" refers to both aryl and heteroaryl groups.

As used herein, "arylene" is a divalent radical of an aromatic group containing 5-12 ring atoms and can contain optional fused rings, which may be saturated, unsaturated, or aromatic. Examples of an arylene groups that are carbocyclic include phenylene, naphthylene, biphenylene, phenanthrylene, and anthracylene. The term "heteroarylene" refers to an arylene containing 1-3 heteroatoms such as nitrogen, oxygen, or sulfur and can contain fused rings. Some examples of heteroarylene groups are pyridylene, furanylene, pyrrolylene, thienylene, thiazolylene, oxazolylene, imidazolylene, indolylene, benzofuranylene, and benzthiazolylene. The term "(hetero)arylene" refers to both arylene and heteroarylene.

Spores can adhere strongly to surfaces such as skin and can be very difficult to remove. Methods for removing spores from surfaces are important because there is a great deal of interest and urgency in preventing the spread of *C. difficile*, particularly in medical settings such as hospitals. Patients in a hospital setting often times develop *C. difficile* infections during or shortly after a course of antibiotics. While it is relatively easy to kill the vegetative form of *C. difficile*, the spore form of *C. difficile*, can be very difficult to kill. New technologies are needed to address the problem of preventing the spread of *C. difficile*, between patients, health care workers, and the environment.

Previously utilized methods or compositions are numerous, and include bleach, alcohol foams and gels, for example. Bleach is a commonly used sporicide, and is effective and recommended by the Centers for Disease Control (CDC) for use in a hospital setting to disinfect environmental surfaces. However, bleach cannot be utilized by patients and health care workers on their skin. Currently, alcohol foams and gels are used by most healthcare workers. These solutions are however not effective at eradicating *C. difficile* spores. The CDC recommendation for healthcare workers and patients affected by *C. difficile* is normal hand washing with soap, water and paper towel. However, it is not always convenient to implement this solution for a health care worker due to the lack of nearby sink access and time. Further, this is an inconvenient solution for the caregiver to implement on a patient with limited mobility.

Dilute bleach or hydrogen peroxide and similar products have been used on hands and have demonstrated the ability to kill spores. While spore kill is important, it is not clear that these solutions are safe for repeated use. For example, a health care worker may wash their hands 30-50 times in a single day, and some up to 75 times a day or more as they wash in and out of patient rooms. Long term toxicity and destruction of host tissues would be a concern for these solutions.

It is therefore extremely important to develop compositions that are safe for repeated use on the skin; reduce spores to a level equivalent to that of the CDC recommended protocol (soap, water and paper towel); and have the ability to kill vegetative bacteria rapidly. Alcohol is used to kill vegetative cells rapidly, but does not kill spores. It would also be useful to have compositions that could be used in various formats including wipes, gels, sprays, etc. Compositions that could be utilized for various aspects of patient care such as hand sanitization, patient bathing, and pre-op care could also be greatly beneficial. Compositions that could be used for patient care as well as environmental cleaning; for example, fragile or expensive equipment/surfaces in a hospital room that may warrant the use of less aggressive tissue friendly chemicals could also be quite useful to the medical community.

Disclosed methods overcome spore adhesion to surfaces, such as the skin, allowing for the spores to be dispersed and transferred into an article, for example a woven, knitted, or nonwoven wipe surface. Disclosed methods include methods of dislodging spores from a surface, methods of removing spores from a surface, or combinations thereof First and Second Compositions Disclosed methods can include at least two steps. Disclosed methods generally include a first step of contacting a surface with a first composition and a second step of contacting the surface with a second composition. Both the first and the second compositions are liquids. At least one and only one of the first or the second composition includes greater than or equal to 60 wt % of at least one alcohol. The first composition, the second composition, or both can include acrylate copolymer particles. The second composition is generally loaded in or on a cationic coated article. The second composition is generally contacted with the surface while at least some of the first composition remains on the surface.

Disclosed methods include a step of contacting the surface with the first composition. This contact can be with the first composition alone or the first composition can be loaded into an article, such as a wipe. Disclosed methods include a step of contacting the surface with a cationic coated article loaded with the second composition. The second composition is a liquid. The second composition may include greater than 60 wt % alcohol, in embodiments where the first composition does not include greater than 60 wt % alcohol. The first composition may include greater than 60 wt % alcohol, in embodiments where the second composition does not include greater than 60 wt % alcohol.

In some embodiments, the second composition includes a greatest amount, based on weight, of water. In some embodiments, at least 80% of the second composition is water based on the total weight of the second composition, at least 90% of the second composition is water based on the total weight of the second composition, at least 95% of the second composition is water based on the total weight of the second composition, or at least 99% of the second composition is water based on the total weight of the second composition.

In some embodiments, the second composition, the first composition or both can include a component that more easily allows the composition to wet a wipe such as a cationic coated wipe, for example a surfactant. Particular illustrative surfactants can include, for example nonionic surfactants such as sorbitan fatty acid esters or more specifically TWEEN®. Additionally, surfactants such as those discussed below with respect to optional components can also be utilized in the second composition.

At least one and only one of the first or the second compositions include greater than or equal to 60 wt % of at least one alcohol. In some embodiments, at least one of the first and second compositions includes alcohol. As such, in some embodiments, the first composition includes alcohol and the second composition does not; in some embodiments, the second composition includes alcohol and the first composition does not; in some embodiments, the first composition includes greater than or equal to 60 wt % of at least one alcohol and the second composition includes less than 60 wt % alcohol; or in some embodiments, the first composition includes less than 60 wt % alcohol and the second composition includes greater than or equal to 60 wt % alcohol.

Acrylate Copolymer Particles

The first composition includes acrylate copolymer particles. The acrylate copolymer particles include or are formed from at least one component having a low glass transition temperature (Tg) and at least one component having a high Tg. As used herein the term high Tg component or low Tg component refers to the glass transition temperature of a homopolymer formed from that component. For example, N-vinyl pyrrolidone would be a high Tg component since polyvinyl pyrrolidone has a Tg of 54° C. while isooctylacrylate (IOA) is a low Tg component (monomer) since a poly (IOA) polymer has a Tg of −58° C. The component or components having a low Tg can be referred to as a low Tg component and the component or components having a high Tg can be referred to as a high Tg component. The low Tg component can be formed from a low Tg monomer and the high Tg component can be formed from a high Tg monomer.

It should be noted that more than one copolymer can be utilized herein. A copolymer can be formed by copolymerization of at least 2 monomers to form a block or random copolymer. A blend of two homopolymer components in a ratio to provide a similar Tg to that of an acrylate copolymer produced from two monomers is not considered a copolymer as used in disclosed compositions. Copolymer particles as that phrase is utilized herein are preferably formed from a single copolymer but blends of two or more copolymers or blends with other homopolymers may be useful. Properties such as shear and adhesion properties, for example, of a blend designed to give a particular Tg may be different than the properties found in a disclosed copolymer having the same particular overall Tg.

An acrylate copolymer as described herein includes at least one acrylate component, or was polymerized from a reaction mixture containing at least one component or monomer, for example at least one acrylic containing monomer. More specifically, disclosed compositions can include acrylate copolymer particles. The acrylate copolymer or acrylate copolymer particles can be described as the reaction product of at least a low Tg monomer and a high Tg monomer. The acrylate copolymer particles can also be described by their particle size. The acrylate copolymer or copolymer particles can be described as the reaction product of a reaction mixture that includes at least one component, e.g., at least one low Tg monomer, at least one high Tg monomer, or combinations thereof, etc.

The amount of the acrylate copolymer in the first composition can also be indicated. In some embodiments, the first composition can include not less than 0.25 wt % acrylate copolymer, not less than 0.5 wt % acrylate copolymer, or not less than 1 wt % acrylate copolymer, or in some embodiments not less than 2 wt % acrylate copolymer based on the total weight of the entire first composition. In some embodiments, the first composition can include not greater than 15 wt % acrylate copolymer, not greater than 5 wt % acrylate copolymer, or in some embodiments not greater than 4 wt % based on the total weight of the entire first composition. In some embodiments, the first composition can include from 1 wt % to 5 wt % acrylate copolymer, or in some embodiments from 2 wt % to 4 wt % acrylate copolymer based on the total weight of the entire first composition.

Acrylate copolymers or more specifically acrylate copolymer particles in the first composition can be described by the monomers used to form the acrylate copolymer. In some embodiments at least one or more monomers having a high Tg and at least one or more monomers having a low Tg can be utilized to form the acrylate copolymer in disclosed compositions. As used herein, a value for the Tg of a monomer is the Tg of a homopolymer polymerized from the particular monomer. The low Tg monomer forms the low Tg component of the acrylate copolymer and the high Tg monomer forms the high Tg component of the acrylate copolymer.

In some embodiments, the at least one or more monomers having a high Tg can be a monomer(s) having a Tg of not less than 40° C., or in some embodiments not less than 60° C. for example. In some embodiments, the at least one or more monomers having a high Tg can be a monomer(s) having a Tg of not greater than 150° C., or not greater than 125° C. for example. In some embodiments, the at least one or more monomers having a high Tg can be a monomer(s) having a Tg from 40° C. to 150° C., or in some embodiments from 60° C. to 125° C., for example. In some embodiments, a high Tg monomer or component can have a Tg of 105° C. In some embodiments, the at least one or more monomers having a low Tg can be a monomer(s) having a Tg of not greater than −30° C., or in some embodiments not greater than −20° C. for example. In some embodiments, the at least one or more monomers having a low Tg can be a monomer(s) having a Tg of not less than −60° C., or not less than −55° C. for example. In some embodiments, the at least one or more monomers having a low Tg can be a monomer(s) having a Tg from −60 to −20° C., for example. In some embodiments, a low Tg monomer or component can have a Tg of −50° C.

Low Tg and high Tg monomers components can also be described by the number of carbons in the monomer. For example, low Tg monomers can include monomers having not less than four (4) alkyl chain carbons. In some embodiments, low Tg monomers can have not greater than 10 carbons. For example, high Tg monomers can include monomers having not greater than three (3) carbons. In some embodiments, high Tg monomers can have not less than one (1) carbon.

Low Tg and high Tg monomers can also be described structurally. In some embodiments, high Tg monomers can be those of formula I below:

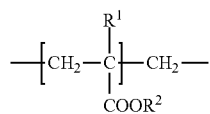

(I)

where $R^1$ is H or —$CH_3$, and $R^2$ is —$CH_3$ or —$CH_2CH_3$. In some embodiments, low Tg monomers can be those of formula II below:

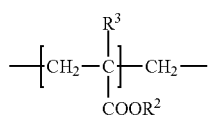

(II)

where $R^3$ is H or —$CH_3$, $R^4$ is —$CH_2(CH_2)$—$CH_3$ where x is an integer from one (1) to twelve (12) and the alkyl chain can be straight or branched. In some embodiments, x can be an integer from two (2) to six (6). In some embodiments, x can be six (6) and the alkyl can be a branched alkyl.

As such, acrylate copolymers formed from at least monomers of formula I and II can be described as follows in formula III.

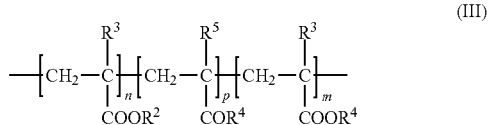

(III)

where $R^1$ is H or —$CH_3$, $R^2$ is H, —$CH_3$ or —$CH_2CH_3$, $R^3$ is H or —$CH_3$, $R^4$ is —$CH_2(CH_2)$—$CH_3$ where x is an integer from one (1) to eight (8) and the alkyl chain can be straight or branched, $R^5$ is H or —$CH_3$, $R^6$ is OH, $NH_2$, $NHCH_3$, $N(CH_3)_2$, —$OCH_2CH_2OH$, m is an integer from 20 to 1,500,000, n is an integer from 20 to 1,500,000, p is an integer from zero (0) to 1,500,000, with the proviso that m is greater than n, and both m and n are greater than p. In some embodiments $R^1$ is —$CH_3$, $R^2$ is —$CH_3$ or —$CH_2CH_3$, and $R^3$ is H. In some embodiments, the optional monomer (the middle structure in the polymeric chain above) can be derived from an acrylamide monomer, an acrylic acid monomer, a pyrrolidone monomer, a N-vinyl pyrrolidone monomer, or other high Tg monomer, or any combination thereof. It should be noted that the order of the monomers listed in the formula above are for illustration purposes only. The monomers may occur in any order in a random or block fashion.

In some illustrative embodiments, low Tg monomers can include for example 2-ethylhexyl acrylate (EHA) that has a Tg of −50° C., butyl acrylate (BA) that has a Tg of −54° C., and isooctylacrylate (IOA) that has a Tg of −58° C., or combinations thereof. In some illustrative embodiments, high Tg monomers can include, for example, methyl methacrylate (MMA) that has a Tg of 105° C., acrylic acid (AA) that has a Tg of 105° C., and hydroxyethylmethacrylate (HEMA) that has a Tg of 55° C. Specific examples of potential polymers that can be utilized as or in useful copolymer particles can include, for example acrylates such as Dermacryl C (polymerized from a mixture of EHA, MMA and AA) commercially available from Akzo Personal Care and Balance 0/55 (polymerized from a mixture of BA and MMA) previously commercially available from Akzo Personal Care.

Copolymer particles useful herein can also include optional components or optional monomers. Some such optional components can include, other polymers and/or monomers that may be used to form copolymer particles. If polymers are utilized to form the copolymer particles, the weight of such polymers are considered monomers when determining the total weight of the reaction mixture. Generally, the composition of the acrylate copolymer particles can include but are not limited to the following polymers: acrylates, polyacrylates, urethanes, polyurethanes, polyesters, polysaccharides, polyolefins, polyamides, polyimides, polyethylenes, polyalkyls, polyols, polystyrenes, polyethers, polyhalides, polynitriles, cellulosics, proteins, triglycerides, polyamino acids, silicone polymers and resins, esters derived from rosin, epoxy resins, shellacs, latexes, or any combinations thereof.

Specific examples of components than can be included in acrylate copolymer particles can include for example PVP K Series (polyvinylpyrrolidone) from International Specialty Products, Luviskol K Series (polyvinylpyrrolidone) from BASF, PVP/VA (vinyl acetate/vinyl pyrrolidone copolymer) from International Specialty Products, for example grades W-735 and S-630, Gantrez (copolymers of methyl vinyl ether/maleic anhydride) from International Specialty Products, Carboset Series (acrylate copolymer) from BF Goodrich, Resyn Series (vinyl acetate/crotonate copolymers) from National Starch and Chemical Corporation, Versatyl Series (acrylate/octylacrylamide copolymers) from National Starch and Chemical Corporation. Airvol (polyvinylalcohol copolymer) from Air Products and Chemicals, for example all commercially available grades like Airvol 103, Airvol 325, Airvol 540, Airvol 523S, Vinex copolymer of vinyl alcohol and poly(oxyalkylene)acrylate from Air Products and Chemicals, for example all commercially available grades such as Vinex 1003, Vinex 2034, Vinex 2144, Vinex 2019, PEOX (polyethyloxazoline) from Polymer Chemistry Innovations, Covacryl A15 and Covacryl E14 by Wackherr, acrylates/ethylhexyl acrylate copolymers (Daitosol 5000SJ by Daito Kasei), butyl acrylate/hydroxypropyl dimethicone acrylate copolymers (Granacrysil BAS by Grant Industries, Inc.), acrylates/$C_{12}$-$C_{22}$ alkylmethacrylate copolymers (Allianz OPT by ISP), isododecane and acrylates copolymers (Giovarez AC-5099M by Phoenix), acrylates/octylacrylamide copolymers (Dermacryl-79 by National Starch & Chemical Company), and sodium polystyrene sulfonates (Flexan 130 by National Starch & Chemical Company), Ganex (vinyl pyrolidinone/Eicosenene copolymer) from ISP, Polectron (vinylpyrrolidinone/styrene copolymer emulsion) from ISP.

Although not bound by any particular theory, suitable components of the acrylate polymers may be selected on the basis of their properties and/or structure. Some acrylates are insoluble in water in their free acid form and, thus, are water resistant. If such water-insoluble acrylates are neutralized with a base to their salt form, water solubility can be significantly increased. The solubility profile of an acrylate polymer may be impacted by the incidence of polar or ionic groups such as acid groups therein. The properties may also be dependent on the kind of base that is used to neutralize the acid functionalities in the polymer. For example, an acrylate polymer with triethanolamine as a neutralizer may have different properties from one neutralized using sodium hydroxide. In one embodiment, an acrylate copolymer may include an acrylate polymer with an alkyl or aralkyl quaternary ammonium salt such as cetyl pyridinium chloride to form an ionic complex with all or part of the acid functionalities. In addition, the optional surfactants that may be used to keep the acrylate emulsion stable may play a role in the final formulation.

Anionic monomers such as acrylic acid (AA) monomer in relatively small concentrations can also be included in reaction mixtures or disclosed compositions. The acid functionalities thereof can be complexed using, for example, cationic compounds such as cationic antimicrobials (e.g. benzalkonium chloride, cetylpyridinium chloride, etc). In addition, primary, secondary, and tertiary amines can be used to neutralize acidic monomers. These amines also may optionally provide antimicrobial activity (e.g. lauryl arginate, chlorhexidine, etc.)

In some embodiments Dermacryl C, Balance O/55 and Avalure 210 may be utilized. Acidic functionalities in these copolymers that are partially neutralized may be useful for spore removal. These particular copolymers form soft flexible coatings that are water-resistant. These polymers have also been designed for removal using soap and water in cosmetic applications. Disclosed compositions may also be advantageously removed from the surface. As a possible use of disclosed compositions is for the skin it could be advantageous to have acceptable cosmetic appeal since there may be repeated contact with hands for example. For instance, undesirable characteristics could include "balling" of the formulation, peeling of dried formulation, causing the skin to feel dry or chapped, etc. Excipients could optionally be added to improve cosmetic properties such as those described above; however, one would have to consider whether such excipients could have a negative effect on the spore removal performance as well as possible antibacterial nature of the composition. The addition of room temperature waxes such as stearic acid, stearyl alcohol, cetyl palmitate, etc. or silicone based emollients such as dimethicone copolyols and dimethicones, for example, may aid in improving such properties.

Useful acrylate copolymers are the reaction product of at least one high Tg monomer and at least one low Tg monomer. In some embodiments, the amount of the at least one low Tg monomer is greater than the amount of the at least one high Tg monomer. In some embodiments the acrylate copolymer is the reaction product of at least 5 wt % of at least one high Tg monomer, at least 10 wt % of at least one high Tg monomer, at least 15 wt % of at least one high Tg monomer, or at least 20 wt % of a high Tg monomer based on the total weight of the reaction mixture that forms the acrylate copolymer. In some embodiments the acrylate copolymer is the reaction product of not greater than 40 wt % of at least one high Tg monomer, not greater than 50 wt % of at least one high Tg monomer, not greater than 60 wt % of a high Tg monomer, not greater than 80 wt % of a high Tg monomer, or in some embodiments not greater than 85 wt % of a high Tg monomer based on the total weight of the reaction mixture that forms the acrylate copolymer. In some embodiments, the acrylate copolymer is the reaction product of from 5 wt % to 80 wt % of at least one high Tg monomer, from 5 wt % to 50 wt % of at least one high Tg monomer, from 20 wt % to 50 wt % of at least one high Tg monomer, or from 20 wt % to 60 wt % of a high Tg monomer based on the total weight of the reaction mixture that forms the acrylate copolymer.

In some embodiments the acrylate copolymer is the reaction product of at least 10 wt % of at least one low Tg monomer, at least 20 wt % of at least one low Tg monomer, at least 25 wt % of at least one low Tg monomer, at least 40 wt % of at least one low Tg monomer, or at least 60 wt % of at least one low Tg monomer based on the total weight of the reaction mixture that forms the acrylate copolymer. In some embodiments the acrylate copolymer is the reaction product of not greater than 80 wt % of at least one low Tg monomer, not greater than 85 wt % of at least one low Tg monomer, or not greater than 90 wt % of at least one low Tg monomer based on the total weight of the reaction mixture that forms the acrylate copolymer. In some embodiments, the acrylate copolymer is the reaction product of from 40 wt % to 90 wt % of at least one low Tg monomer, from 20 wt % to 80 wt % of at least one low Tg monomer, from 40 wt % to 80 wt % of at least one low Tg monomer, or from 60 wt % to 80 wt % of at least one low Tg monomer based on the total weight of the reaction mixture that forms the acrylate copolymer.

In some embodiments, the acrylate copolymer or the reaction mixture that forms the acrylate copolymer can be described by the total minimum amount of the at least one low Tg and the at least one high Tg monomer contained therein. For example a reaction mixture can include at least 25 wt % of all low Tg and high Tg monomers in a reaction mixture, or include at least 30 wt % of all low Tg and high Tg monomers in a reaction mixture based on the total of the monomers in the reaction mixture.

Acrylate copolymers in disclosed compositions may be more specifically described as acrylate copolymer particles dispersed in the composition. As such, the acrylate copolymer particles can be described by their particle size. In some embodiments, acrylate copolymer particles can have a number average diameter of not less than 100 nanometers (nm), or in some embodiments not less than 200 nm. In some embodiments, acrylate copolymer particles can have a number average diameter of not greater than 500 nm. The size of the acrylate copolymer particles may be relevant in effecting or at least partially effecting spore removal. In some embodiments, acrylate copolymer particles may have a number average diameter in the micrometer (or micron) range.

In some embodiments, compositions that include acrylate copolymer particles can be described as stable dispersions. A "stable dispersion" as utilized herein refers to a composition in which particles remain dispersed in solution without falling out or "crashing out" of solution (e.g. flocculating or settling). In some embodiments, the first composition can be described as a hydroalcoholic solution.

The phrase "hydroalcoholic solution" refers to a composition or solution that includes at least water and an alcohol. In some embodiments, acrylate copolymer particles can be dispersed in a hydroalcoholic solution. In some embodiments, a useful hydroalcoholic solution can include not less than 1 percent by weight (wt %) water, or in some embodiments not less than 5 wt % water based on the total weight of the hydroalcoholic solution. In some embodiments, a useful hydroalcoholic solution can include not greater than 15 wt % water based on the total weight of the hydroalcoholic solution. In some embodiments, a useful hydroalcoholic solution can include not less than 30 wt % alcohol based on the total weight of the hydroalcoholic solution. In some embodiments a useful hydroalcoholic solution can include not greater than 85 wt % alcohol, not greater than 95 wt % alcohol, or not greater than 99% alcohol based on the total weight of the hydroalcoholic solution.

In some embodiments, the step of contacting a composition that includes acrylate copolymer particles with the surface can cause the copolymer particles to become associated with spores on the surface. It is thought, but not relied upon that the copolymer particles become associated with the outer surface of the spores. For example, it may be that the copolymer particles become adhered to the outer surface of the spores. Once the copolymer particles are associated with the spores the spores may be more easily removed from the surface than if they were not associated with the copolymer particles.

It is thought, but not relied upon that the at least one low Tg component of the copolymer particles assists the copolymer particle with adhering to the spores and the at least one high Tg component of the copolymer particles assists the composition in removing the spore from the surface. Excess amounts of the at least one low Tg component or insufficient amounts of the at least one high Tg component may make it more difficult for the spores to be removed from the surface even though they are associated with the copolymer particles. Similarly, insufficient amounts of the at least one low Tg component or excess amounts of the at least one high Tg component may make it more difficult for the copolymer particle to adhere to the spores. The ratio of the at least one low Tg component to the at least one high Tg component may therefore be important to provide both adherence to the spore and removal of the spore from the surface. Disclosed compositions should allow for preferential bonding to the surface of the spore rather than to the surface on which the spore is located. In addition, disclosed compositions should weaken the interaction of the spores to the surface.

Alcohol

Disclosed methods utilize two compositions, a first composition and a second composition. At least one and only one of the first and the second compositions include greater than or equal to 60 wt % of at least one alcohol. The one of the first and second compositions that includes less than 60 wt % of at least one alcohol can include water as a solvent. The one of the first and second compositions that includes greater than or equal to 60 wt % of at least one alcohol can include water as a co-solvent. In some embodiments, the one of the first and second compositions that includes less than 60 wt % of at least one alcohol includes water as the main component (based on weight) of the solvent. In some embodiments, at least one and only one of the first and second compositions include a substantial (e.g., greater than or equal to 1 wt % or greater than or equal to 2 wt %) amount of alcohol. In some embodiments, at least one and only one of the first and second compositions include any amount of alcohol. In some embodiments, one of the compositions can include a minimal amount of at least one alcohol, e.g. 0.01 wt %, and the other composition can include at least 60 wt % of at least one alcohol.

Any kind of alkyl monofunctional alcohol can be utilized as the alcohol(s) in the first or the second composition. In some embodiments, a lower hydrocarbon chain alcohol such as a $C_2$-$C_5$ alcohol can be utilized. In some embodiments the alcohol is chosen from ethanol and isopropanol, and in some embodiments the alcohol includes ethanol. Ethanol may be useful because it may provide a broad spectrum and quick kill of microbes and has an odor acceptable to consumers such as doctors, nurses and clinicians. Propyl alcohol (1-propanol) may also be used. A blend of two or more lower alcohols may also be utilized. The lower alcohols may be denatured, such as for example, denatured ethanol including SDA-3C (commercially available from Eastman Chemical, Kingsport, Tenn.). Co-solvents may be further included in the composition with the lower alcohol. Considering likely applications contemplated, suitable co-solvents can include for example acetone, hydrocarbons such as isooctane, glycols, ketones, ethers, and short chain esters.

In some embodiments, the amount of alcohol in the compositions can also be considered. The amount of alcohol in the compositions may be relevant because the alcohol content can provide bacteria killing properties, as well as spore removal via disclosed methods. In some embodiments, first or second compositions, or both can have at least 30 wt % alcohol based on the total weight of the entire first or second composition respectively (but only one of the compositions has greater than or equal to 60 wt %).

Alcohol amounts of not greater than 30 wt % may assist or aid in decreasing drying times of surfaces, e.g., skin surfaces, upon which the composition containing the 30 wt % alcohol is dispensed. Further, this amount of alcohol may not adversely or may not sufficiently adversely affect spore removal in this step. Including an amount of alcohol advantageous to drying time can be especially beneficial in a method where the first step of the method includes a first composition having an alcohol amount of greater than or equal to 60 wt %.

In some embodiments, one and only one of first and second compositions can have not less than 60 wt % alcohol, or in some embodiments not less than 70 wt % alcohol based on the total weight of the entire first or second composition respectively. In some embodiments, one and only one of first or second compositions can have not greater than 85 wt % alcohol, not greater than 95 wt % alcohol, or not greater than 98 wt % alcohol based on the total weight of the entire first or second composition respectively. In some embodiments one and only one of first or second compositions can have from 60 wt % to 70 wt % alcohol in the entire first or second composition based on the total weight of the entire first or second composition. In some embodiments, first or second compositions that also include acrylate copolymer particles can have from 30 wt % to 85 wt % alcohol in the entire first or second composition based on the total weight of the entire first or second composition. In some embodiments, first or second compositions that do not include acrylate copolymer particles can have from 30 wt % to 95 wt % alcohol in the entire first or second composition based on the total weight of the entire first or second composition.

In some embodiments, the first composition can include an alcohol. In some such embodiments, the first composition can be described as a hydroalcoholic solution that contains acrylate copolymer particles dispersed therein.

Cationic Coated Article

Disclosed methods include a second step of contacting the surface with an article loaded with a second composition. Disclosed articles generally include a substrate that includes a cationic coating. The cationic coated substrate of the article is loaded with the second composition. The substrate can be porous and can include sponge, nonwoven fabric, or woven fabric, for example. In some embodiments, the article can be a wipe that includes a cationic coated substrate onto or into which the second composition is loaded.

The substrate may be in any suitable form for example. Some suitable substrates are woven or non-woven fabrics that are in the form of a sheet. The sheet can have any desired size and shape. Other suitable substrates are sponges that can have any desired size or shape. The substrates are usually porous. Suitable substrates are typically flexible so that the wipe can easily conform and contact various surfaces such as those that are not flat.

The substrate may be formed from any suitable thermoplastic or thermoset material. The material may be an organic polymeric material. Suitable organic polymeric materials include, but are not limited to, poly(meth)acrylates, poly(meth)acrylamides, polyolefins, poly(isoprenes), poly(butadienes), fluorinated polymers, chlorinated polymers, polyamides, polyimides, polyethers, poly(ether sulfones), poly(sulfones), poly(vinyl acetates), copolymers of vinyl acetate, such as poly(ethylene)-co-poly(vinyl alcohol), poly(phosphazenes), poly(vinyl esters), poly(vinyl ethers), poly(vinyl alcohols), poly(carbonates), polyurethanes, and cellulosic materials.

Suitable polyolefins include, but are not limited to, poly (ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly (iminoadipoyliminohexamethylene), poly(iminoadipoyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

Suitable cellulosic materials include cotton, rayon, and blends thereof.

In some embodiments, the substrate is formed from propylene polymers (e.g., homopolymer or copolymers). Polypropylene polymers, particularly polypropylene homopolymers, may be especially useful for some applications due to properties such as non-toxicity, inertness, low cost, and the ease with which it can be extruded, molded, and formed into articles. Polypropylene polymers can be formed, for example, into porous sheets of woven or nonwoven fibers.

Some substrates are nonwoven fabrics. As used herein, the term "nonwoven fabric" refers to a fabric or web that has a structure of individual fibers or filaments that are randomly and/or unidirectionally interlaid in a mat-like fashion. The individual fibers or threads are not interlaid in an identifiable pattern as in a knitted or woven fabric. Examples of suitable nonwoven fabrics include, but are not limited to, melt-blown fabrics, spun-bond fabrics, carded fabrics, wetlaid fabrics, and air-laid fabrics.

Spun-bonded fibers are typically small diameter fibers that are formed by extruding molten thermoplastic polymer as filaments from a plurality of fine, usually circular capillaries of a spinneret with the diameter of the extruded fibers being rapidly reduced. Melt-blown fibers are typically formed by extruding the molten thermoplastic material through a plurality of fine, usually circular, die capillaries as molten threads or filaments into a high velocity, usually heated gas (e.g., air) stream which attenuates the filaments of molten thermoplastic material to reduce their diameter. Thereafter, the melt-blown fibers are carried by the high velocity gas stream and are deposited on a collecting surface to from a fabric of randomly disbursed melt-blown fibers. Any of the non-woven fabrics may be made from a single type of fiber or two or more fibers that differ in the type of thermoplastic polymer and/or thickness.

Wet-laid fibers can be formed into sheets by forming a slurry that contains a) fibers and b) a suspending liquid such as water, a water-miscible organic solvent, or a mixture thereof. The slurry is placed in mold or deposited in a layer. The suspending liquid is removed to form a sheet or mat. The sheet or mat is then dried. In some embodiments, a polymeric binder is included in the dispersion. In other embodiments, a polymeric binder can be applied after formation of a sheet or mat. The polymeric binder is often a latex polymer.

Further details on the manufacturing method of nonwoven fabrics may be found in Wente, Superfine Thermoplastic Fibers, 48 INDUS. ENG. CHEM. 1342(1956), or in Wente et al., Manufacture Of Superfine Organic Fibers, (Naval Research Laboratories Report No. 4364, 1954).

The substrate includes a cationic coating or is coated with a composition that is cationic in nature. In some embodiments, the coatings can include chitosan, or polymers such as polyethylenimine (PEI), or quaternized cellulose, silanes, or guar gums, guanidinyl coatings, or combinations thereof. In some embodiments, the coatings can include guanidinyl coatings.

In some embodiments, cationic coatings can include a guanidinyl-containing polymer that can be bound to the substrate. Although any guanidinyl-containing polymer can be used in the cationic coating, in some embodiments, a polymer of Formula (I) can be utilized.

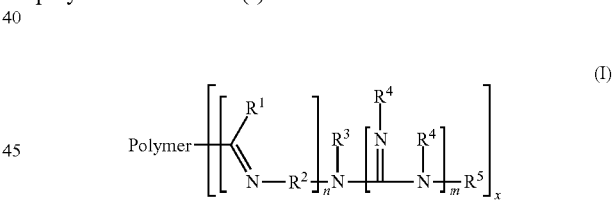

In Formula (I), the group $R^1$ is hydrogen, $C_1$-$C_{12}$ (hetero) alkyl, or $C_5$-$C_{12}$ (hetero)aryl, or a residue of the polymer chain. The group $R^2$ is a covalent bond, a $C_2$-$C_{12}$ (hetero) alkylene, or a $C_5$-$C_{12}$ (hetero)arylene. The group $R^3$ is H, $C_1$-$C_{12}$ (hetero)alkyl, or $C_5$-$C_{12}$ (hetero)aryl, or can be a residue of the polymer chain when n is 0. Each group $R^4$ is independently hydrogen, $C_1$-$C_{12}$ (hetero)alkyl, or $C_5$-$C_{12}$ (hetero)aryl. The group $R^5$ is hydrogen, $C_1$-$C_{12}$ (hetero) alkyl, $C_5$-$C_{12}$ (hetero)aryl, or —$N(R^4)_2$. The variable n is equal to 0 or 1 depending on the precursor polymer used to form the guanidinyl-containing polymer. The variable m is equal to 1 or 2 depending on whether the cationic group is a guanidinyl or biguanidinyl group. The term "Polymer" in Formula (I) refers to all portions of the guanidinyl-containing polymer except the x groups of formula —[C($R^1$)=N—$R^2$-1N($R^3$)—[C(=$NR^4$)—$NR^4$]$_m R^5$—]. The term x is a variable equal to at least 1.

Most guanidinyl-containing polymers have more than one guanidinyl group. The number of guanidinyl groups can be varied depending the method used to prepare the guanidinyl-containing polymer. For example, the number of guanidinyl groups can depend on the choice of precursor polymer selected for reacting with a suitable guanylating agent. In some embodiments, the variable x can be up to 1000, up to 500, up to 100, up to 80, up to 60, up to 40, up to 20, or up to 10.

The guanidinyl-containing polymer of Formula (I) is often the reaction product of (a) a precursor polymer and (b) a suitable guanylating agent. The precursor polymer is often an amino-containing polymer or a carbonyl-containing polymer. When the precursor polymer is an amino-containing polymer, the variable n in Formula (I) is typically equal to 0. When the precursor polymer is a carbonyl-containing polymer, the variable n is equal to 1. If the guanylating agent contains a guanidinyl group or a precursor of a guanidinyl group, the variable m in Formula (I) is equal to 1. If the guanylating agent contains a biguanidinyl group or a precursor of a biguanidinyl group, the variable m in Formula (I) is equal to 2.

In embodiments where n is 0, the base polymer of the guanidinyl-containing polymer is often prepared by reaction of a suitable guanylating agent and an amino-containing polymer. In other embodiments, where n is 1, the guanidinyl-containing polymer is often prepared by reaction of a suitable guanylating agent and a carbonyl-containing polymer.

In those embodiments where n is 0 and the precursor polymer is an amino-containing polymer, the structure of the guanidinyl-containing polymer of Formula (I) can also be written more simply as the structure of Formula (II).

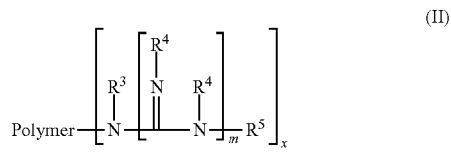

In Formula (II), the group $R^3$ is hydrogen, $C_1$-$C_{12}$ (hetero)alkyl, or $C_5$-$C_{12}$ (hetero)aryl, or can be a residue of the polymer chain. When the guanidinyl group is part of a pendant group, $R^3$ is hydrogen, $C_1$-$C_{12}$ (hetero)alkyl, or $C_5$-$C_{12}$ (hetero)aryl. Each $R^4$ is independently hydrogen, $C_1$-$C_{12}$ (hetero)alkyl, or $C_5$-$C_{12}$ (hetero)aryl. The group $R^5$ is hydrogen, $C_1$-$C_{12}$ (hetero)alkyl, or $C_5$-$C_{12}$ (hetero)aryl, or —$N(R^4)_2$. The variable m is equal to 1 or 2. The term "Polymer" in Formula (II) refers to all portions of the guanidinyl-containing polymer except the x groups of formula —$N(R^3)$—[C(=$NR^4$)—$NR^4$]$_m R^5$—. The term x is a variable equal to at least 1.

The amino-containing polymer used as a precursor polymer to prepare a guanidinyl-containing polymer of Formula (II) can be represented by the formula Polymer-$N(R^3)H$. As noted above, however, the amino-containing polymer typically has many groups —$N(R^3)H$ but Formula (I) shows only one for ease of discussion purposes only. The —$N(R^3)H$ groups can be a primary or secondary amino group and can be part of a pendant group or part of the backbone of the precursor polymer. The amino-containing polymers can be synthesized or can be naturally occurring biopolymers. Suitable amino-containing polymers can be prepared by chain growth or step growth polymerization procedures with amino-containing monomers. These monomers can also, if desired, be copolymerized with other monomers without an amino-containing group. Additionally, the amino-containing polymers can be obtained by grafting primary or secondary amine groups using an appropriate grafting technique.

In some embodiments, useful amino-containing polymers are polyamines that are water soluble or water-dispersible. As used herein, the term "water soluble" refers to a material that can be dissolved in water. The solubility is typically at least about 0.1 gram per milliliter of water. As used herein, the term "water dispersible" refers to a material that is not water soluble but that can be emulsified or suspended in water.

Examples of amino-containing polymers suitable for use, which are prepared by chain growth polymerization include, but are not limited to, polyvinylamine, poly(N-methylvinylamine), polyallylamine, polyallylmethylamine, polydiallylamine, poly(-aminomethylstyrene), poly(4-aminostyrene), poly(acrylamide-co-methylaminopropylacrylamide), and poly(acrylamide-co-aminoethylmethacrylate).

Examples of amino polymers suitable for use, which are prepared by step growth polymerization include, but are not limited to, polyethylenimine, polypropylenimme, polylysine, polyaminoamides, polydimethylamine-epichlorohydrin-ethylenediamine, and any of a number of polyaminosiloxanes, which can be prepared from monomers such as aminopropyltriethoxysilane, N-(2-aminoethyl)-3-aminopropyltrimethoxysilane, N-trimethoxysilylpropyl-N-methylamine, and bis(trimethoxysilylpropyl)amine.

Other useful amino-containing polymers that have primary or secondary amino end groups include, but are not limited to, dendrimers (hyperbranched polymers) formed from polyamidoamine (PAMAM) and polypropylenimme. Exemplary dendrimeric materials formed from PAMAM are commercially available under the trade designation "STARBURST (PAMAM) dendrimer" (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical (Milwaukee, Wis.). Dendrimeric materials formed from polypropylenimme are commercially available under the trade designation "DAB-Am" from Aldrich Chemical. For example, DAB-Am-4 is a generation 1 polypropylenimme tetraamine dendrimer with 4 primary amino groups, DAB-Am-8 is a generation 2 polypropylenimme octaamine dendrimer with 8 primary amino groups, DAB-Am-16 is a generation 3 polypropylenimme hexadecaamine with 16 primary amino groups, DAB-Am-32 is a generation 4 polypropylenimme dotriacontaamine dendrimer with 32 primary amino groups, and DAB-Am-64 is a generation 5 polypropylenimme tetrahexacontaamine dendrimer with 64 primary amino groups.

Examples of suitable amino-containing polymers that are biopolymers include chitosan as well as starch that is grafted with reagents such as methylaminoethylchloride.

Still other examples of amino-containing polymers include polyacrylamide homo- or copolymers and amino-containing polyacrylate homo- or copolymers prepared with a monomer composition containing an amino-containing monomer such as an aminoalkyl(meth)acrylate, (meth)acrylamidoalkylamine, and diallylamine.

For some wipes, the preferred amino-containing polymers include polyaminoamides, polyethyleneimine, polyvinylamine, polyallylamine, and polydiallylamine.

Suitable commercially available amino-containing polymers include, but are not limited to, polyamidoamines that are available under the trade designations ANQUAMINE (e.g., ANQUAMINE 360, 401, 419, 456, and 701) from Air Products and Chemicals (Allentown, Pa.), polyethylenimine polymers that are available under the trade designation LUPASOL (e.g., LUPASOL FG, PR 8515, Waterfree, P, and PS) from BASF Corporation (Resselaer, N.Y.), polyethylenimine polymers such as those available under the trade designation CORCAT P-600 from EIT Company (Lake Wylie, S.C.), and polyamide resins such as those available from Cognis Corporation (Cincinnati, Ohio) under the traded designation VERSAMID series of resins that are formed by reacting a dimerized unsaturated fatty acid with alkylene polyamines.

Guanidinyl-containing polymers can be prepared by reaction of the amino-containing polymer precursor with a guanylating agent. Although all the amino groups of the amino-containing polymer can be reacted with the guanylating agent, there are often some unreacted amino groups from the amino-containing polymer precursor remaining in the guanidinyl-containing polymer. Typically, at least 0.1 mole percent, at least 0.5 mole percent, at least 1 mole percent, at least 2 mole percent, at least 10 mole percent, at least 20 mole percent, or at least 50 mole percent of the amino groups in the amino-containing polymer precursor are reacted with the guanylating agent. Up to 100 mole percent, up to 90 mole percent, up to 80 mole percent, or up to 60 mole percent of the amino groups can be reacted with the guanylating agent. For example, the guanylating agent can be used in amounts sufficient to functionalize 0.1 to 100 mole percent, 0.5 to 90 mole percent, 1 to 90 mole percent, 1 to 80 mole percent, 1 to 60 mole percent, 2 to 50 mole percent, 2 to 25 mole percent, or 2 to 10 mole percent of the amino groups in the amino-containing polymer.

Known guanylating agents for reaction with an amino-containing polymer precursor include, but are not limited to, cyanamide; O-alkylisourea salts such as O-methylisourea sulfate, O-methylisourea hydrogen sulfate, O-methylisourea acetate, O-ethylisourea hydrogen sulfate, and O-ethylisourea hydrochloride; chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride; and carbodiimides such as dicyclohexylcarbodiimide, N-ethyl-N'-(3-dimethylaminopropyl)carbodiimide, and diisopropylcarbodiimide. The amino-containing polymer may also be acylated with guanidino-functional carboxylic acids such as guanidinoacetic acid and 4-guanidinobutyric acid in the presence of activating agents such as EDC (N-[3-(dimethylamino)propyl]-3-ethylcarbodiimide hydrochloride), or EEDQ (2-ethoxy-1-ethoxycarbonyl-1,2-dihydroquinoline). Additionally, the guanidinyl-containing polymer may be prepared by alkylation with chloroacetone guanyl hydrazone, as described in U.S. Pat. No. 5,712,027 (Ali et al.).

Guanylating agents for the preparation of biguanide-containing polymers include sodium dicyanamide, dicyanodiamide and substituted cyanoguanidines such as $N^3$-p-chlorophenyl-N'-cyanoguanidine, $N^3$-phenyl-N'-cyanoguanidine, $N^3$-alpha-naphthyl-N'-cyanoguanidine, $N^3$-methyl-N'-cyanoguanidine, $N^3,N^3$-dimethyl-N'-cyanoguanidine, $N^3$-(2-hydroxyethyl)-N'-cyanoguanidine, and $N^3$-butyl-N'-cyanoguanidine. Alkylene- and arylenebiscyanoguanidines may be utilized to prepare biguanide functional polymers by chain extension reactions. The preparation of cyanoguanidines and biscyanoguanidines is described in detail in Rose, F. L. and Swain, G. J. Chem Soc, 1956, pp. 4422-4425. Other useful guanylating reagents are described by Alan R. Katritzky et al., Comprehensive Organic Functional Group Transformation, Vol. 6, p. 640.

The guanidinyl-containing polymer formed by reaction of an amino-containing polymer precursor and a guanylating agent will have pendent or catenary guanidinyl groups of the Formula (III).

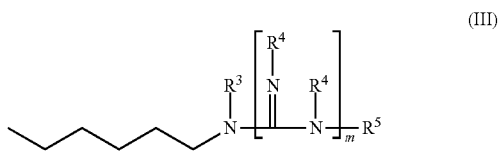

In Formula (III), the groups $R^3$, $R^4$, and $R^5$ and the variable m are the same as defined above. The wavy line attached to the $N(R^3)$ group shows the position of attachment the group to the rest of the polymeric material. In most embodiments, the group of Formula (III) is in a pendant group of the guanidinyl-containing polymer.

In some embodiments, it may be advantageous to react the amino-containing polymer precursor to provide other ligands or groups in addition to the guanidinyl-containing group. For example, it may be useful to include a hydrophobic ligand, an ionic ligand, or a hydrogen bonding ligand. This can be particularly advantageous for the removal of certain microorganisms during the wiping of a microorganism-contaminated surface.

The additional ligands can be readily incorporated into the amino-containing polymers by alkylation or acylation procedures well known in the art. For example amino groups of the amino-containing polymer can be reacted using halide, sulfonate, and sulfate displacement reactions or using epoxide ring opening reactions. Useful alkylating agents for these reactions include, for example, dimethylsulfate, butyl bromide, butyl chloride, benzyl bromide, dodecyl bromide, 2-chloroethanol, bromoacetic acid, 2-chloroethyltrimethylammonium chloride, styrene oxide, glycidyl hexadecyl ether, glycidyltrimethylammonium chloride, and glycidyl phenyl ether. Useful acylating agents include, for example, acid chlorides and anhydrides such as benzoyl chloride, acetic anhydride, succinic anhydride, and decanoyl chloride, and isocyanates such as trimethylsilylisocyanate, phenyl isocyanate, butyl isocyanate, and butyl isothiocyanate. In such embodiments 0.1 to 20 mole percent, preferably 2 to 10 mole percent, of the available amino groups of the amino-containing polymer may be alkylated and/or acylated.

The guanidinyl-containing polymer can be crosslinked. The amino-containing polymer can be crosslinked prior to reaction with the guanylating agent. Alternatively, the guanidinyl-containing polymer can be crosslinked by reaction of a crosslinker with remaining amino groups from the amino-containing polymer precursor or with some of the guanidinyl groups. Suitable crosslinkers include amine-reactive compounds such as bis- and polyaldehydes such as glutaraldehyde, bis- and polygylcidylethers such as butanedioldiglycidylether and ethyleneglycoldiglycidylether, polycarboxylic acids and their derivatives (e.g., acid chlorides), polyisocyanates, formaldehyde-based crosslmkers such as hydroxymethyl and alkoxymethyl functional crosslmkers, such as those derived from urea or melamine, and amine-reactive silanes, such as 3-glycidoxypropyltrimethoxysilane, 3-glycidoxypropyltriethoxysilane, 5,6-epoxyhexyltriethoxysilane, (p-chloromethyl)phenyltrimethoxysilane, chloromethyltriethoxysilane, 3-isocyanatopropyltriethoxysilane, and 3-isothiocyanatopropyltriethoxysilane.

In other embodiments, the guanidinyl-containing polymer is of Formula (IV), which corresponds to Formula (I) where n is equal to 1.

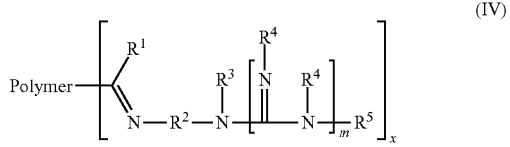

In Formula (IV), the group $R^1$ is hydrogen, $C_1$-$C_{12}$ (hetero)alkyl, or $C_5$-$C_{12}$ (hetero)aryl, or a residue of the polymer chain. If the guanidinyl-containing group is the reaction product of a guanylating agent and a carbonyl group that is part of the backbone of the polymer, $R^1$ is a residue of the polymer chain. Group $R^2$ is a covalent bond, a $C_2$-$C_{12}$ (hetero)alkylene, or a $C_5$-$C_{12}$ (hetero)arylene. Group $R^3$ is hydrogen, $C_1$-$C_{12}$ (hetero)alkyl, or $C_5$-$C_{12}$ (hetero)aryl. Each $R^4$ is independently H, $C_1$-$C_{12}$ (hetero)alkyl, or $C_5$-$C_{12}$ (hetero)aryl. Group $R^5$ is hydrogen, $C_1$-$C_{12}$ (hetero)alkyl, or $C_5$-$C_{12}$ (hetero)aryl, or —$N(R^4)_2$-. The variable m is equal to 1 or 2. The term "Polymer" in Formula (I) refers to all portions of the guanidinyl-containing polymer except the x groups of formula —$C(R^1)$=N—$R^2$—$N(R^3)$—[C(=$NR^4$)—$NR^4]_m R^5$—. The term x is a variable equal to at least 1.

Guanidinyl-containing polymers of Formula (IV) are the reaction product of a carbonyl-containing polymer and a suitable guanylating agent for reaction with a carbonyl group. The carbonyl-containing polymer used as a precursor polymer to prepare a guanidinyl-containing polymer of Formula (IV) can be represented by the formula Polymer-$C(O)$—$R^1$ The carbonyl-containing polymer precursor typically has many groups —$C(O)$—$R^1$ but Formula (IV) shows only one for ease of discussion purposes only. The carbonyl group —$C(O)$—$R^1$ is an aldehyde group (when $R^1$ is hydrogen) or a ketone groups (when $R^1$ is a (hetero)alkyl or (hetero)aryl). Although the carbonyl-group can be part of the polymeric backbone or part of a pendant group from the polymeric backbone, it is typically in a pendant group.

In some embodiments, the carbonyl-containing polymer is the polymerized product of a monomer composition that includes an ethylenically unsaturated monomer having a carbonyl group, preferably a ketone group. Suitable monomers having a carbonyl group include, but are not limited to, acrolein, vinyl methyl ketone, vinyl ethyl ketone, vinyl isobutyl ketone, isopropenyl methyl ketone, vinyl phenyl ketone, diacetone (meth)acrylamide, acetonyl acrylate, and acetoacetoxyethyl (meth)acrylate.

In other embodiments, the carbonyl-containing polymer is the polymerized product of a monomer composition that includes carbon monoxide and one or more ethylenically unsaturated monomer (i.e., the carbonyl-containing polymer is a carbon monoxide copolymers). An example of a carbon monoxide containing copolymer is ELVALOY 741, a terpolymer of ethylene/vinyl acetate/carbon monoxide from DuPont (Wilmington, Del., USA).

In addition to carbon monoxide and/or an ethylenically unsaturated monomer with a carbonyl group (e.g., a ketone group), the monomer composition used to form that carbonyl-containing polymer can optionally further comprise ethylenically unsaturated hydrophilic monomer units. As used herein, "hydrophilic monomers" are those polymerizable monomers having water miscibility (water in monomer) of at least 1 weight percent preferably at least 5 weight percent without reaching a cloud point, and contain no functional groups that would interfere with the binding of biological substances to the ligand group. The carbonyl-containing polymer may include, for example, 0 to 90 weight percent of the hydrophilic monomers in the monomer composition. If present, the hydrophilic monomer can be present in an amount in a range of 1 to 90 weight percent, 1 to 75 weight percent, 1 to 50 weight percent, 1 to 25 weight percent, or 1 to 10 weight percent based on based a total weight of the monomer composition.

The hydrophilic groups of the hydrophilic monomers may be neutral, have a positive charge, a negative charge, or a combination thereof. Hydrophilic monomers with an ionic group can be neutral or charged depending on the pH conditions. Hydrophilic monomers are typically used to impart a desired hydrophilicity (i.e. water solubility or dispersibility) to the carbonyl-containing polymer. A negatively charged hydrophilic monomer may be included as long as it is in small enough amounts that it doesn't interfere with the binding interaction of the guanidinyl group.

Some exemplary hydrophilic monomers that are capable of providing a positive charge are amino (meth)acrylates or amino (meth)acrylamides of Formula (V) or quaternary ammonium salts thereof. The counter ions of the quaternary ammonium salts are often halides, sulfates, phosphates, nitrates, and the like.

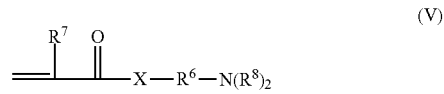

In Formula (V), the group X is oxy (i.e., —O—) or —$NR^3$— where $R^3$ is hydrogen, $C_1$-$C_{12}$ (hetero)alkyl, or $C_5$-$C_{12}$ (hetero)aryl. The group $R^6$ is a $C_2$ to $C_{10}$ alkylene, preferably a $C_2$-$C_6$ alkylene. The group $R^7$ is independently hydrogen or methyl. Each $R^8$ is independently hydrogen, alkyl, hydroxyalkyl (i.e., an alkyl substituted with a hydroxy), or aminoalkyl (i.e., an alkyl substituted with an amino). Alternatively, the two $R^8$ groups taken together with the nitrogen atom to which they are attached can form a heterocyclic group that is aromatic, partially unsaturated (i.e., unsaturated but not aromatic), or saturated, wherein the heterocyclic group can optionally be fused to a second ring that is aromatic (e.g., benzene), partially unsaturated (e.g., cyclohexene), or saturated (e.g., cyclohexane).

It will be understood with respect to Formula (V) that the depicted ethylenically unsaturated(meth)acryloyl group ($CH_2$=$C(R^7)$—$C(O)$— group) may be replaced by another ethylenically unsaturated group of reduced reactivity, such as vinyl, vinyloxy, allyl, allyloxy, and acetylenyl.

In some embodiments of Formula (V), both $R^8$ groups are hydrogen. In other embodiments, one $R^8$ group is hydrogen and the other is an alkyl having 1 to 10, 1 to 6, or 1 to 4 carbon atoms. In still other embodiments, at least one of $R^8$ groups is a hydroxy alkyl or an amino alkyl that have 1 to 10, 1 to 6, or 1 to 4 carbon atoms with the hydroxy or amino group being positioned on any of the carbon atoms of the alkyl group. In yet other embodiments, the $R^8$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to imidazolyl. The heterocyclic group can be fused to an additional ring such as a benzene, cyclohexene, or cyclohexane. Exemplary heterocyclic groups fused to an additional ring include, but are not limited to, benzoimidazolyl.

Illustrative amino acrylates (i.e., "X" in Formula (V) is oxy) include N,N-dialkylaminoalkyl (meth)acrylates such as, for example, N,N-dimethylaminoethyl(meth)acrylate, N,N-dimethylaminoethylacrylate, N,N-diethylaminoethylacrylate, N,N-dimethylaminopropyl(meth)acrylate, N-tert-butylaminopropyl(meth)acrylate, and the like.

Illustrative amino (meth)acrylamides (i.e., "X" in Formula (V) is —$NR^3$—) include, for example, N-(3-aminopropyl)methacrylamide, N-(3-aminopropyl)acrylamide, N-[3-(dimethylamino)propyl]methacrylamide, N-[3-(dimethylamino)propyl]acrylamide, N-(3-imidazolylpropyl)methacrylamide, N-(3-imidazolylpropyl)acrylamide, N-(2-imidazolylethyl)methacrylamide, N-(1,1-dimethyl-3-imidazolylpropyl)methacrylamide, N-(1,1-dimethyl-3-imidazolylpropyl)acrylamide, N-(3-benzimidazolylpropyl)acrylamide, and N-(3-benzimidazolylpropyl)methacrylamide.

Illustrative quaternary salts of the monomers of Formula (V) include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other monomers that can provide positively charged groups to the polymer include the dialkylaminoalkylamine adducts of alkenylazlactones (e.g., 2-(diethylamino)ethylamine, (2-aminoethyl)trimethylammonium chloride, and 3-(dimethylamino)propylamine adducts of vinyldimethylazlactone) and diallylamine monomers (e.g., diallylammonium chloride and diallyldimethylammonium chloride).

In some preferred embodiments, the optional hydrophilic monomer may have an ethylenically unsaturated group such as a (meth)acryloyl group and a poly(alkylene oxide) group. For example, the hydrophilic monomer can be a poly(alkylene oxide) mono(meth)acrylate compounds, where the terminus is a hydroxy group, or an alkyl ether group. Such monomers are of the general Formula (VI).

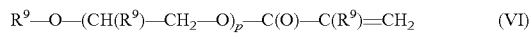

$$R^9\text{—O—}(CH(R^9)\text{—}CH_2\text{—O})_p\text{—}C(O)\text{—}C(R^9)\text{=}CH_2 \quad \text{(VI)}$$

In Formula (VI), each $R^9$ is independently hydrogen or a $C_1$-$C_4$ alkyl. The variable p is at least 2 such as, for example, 2 to 100, 2 to 50, 2 to 20, or 2 to 10.

In one embodiment, the poly(alkylene oxide) group (depicted as —(CH($R^9$)—$CH_2$—O)$_p$—) is a poly(ethylene oxide). In another embodiment, the poly(alkylene oxide) group is a poly(ethylene oxide-co-propylene oxide). Such copolymers may be block copolymers, random copolymers, or gradient copolymers.

Other representative examples of suitable hydrophilic monomers include but are not limited to acrylic acid; methacrylic acid; 2-acrylamido-2-methyl-1-propanesulfonic acid; 2-hydroxyethyl (meth)acrylate; N-vinylpyrrolidone; N-vinylcaprolactam; acrylamide; mono- or di-N-alkyl substituted acrylamide; t-butyl acrylamide; dimethylacrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof. Preferred hydrophilic monomers include those selected from the group consisting of dimethylacrylamide, 2-hydroxyethyl (meth)acrylate, and N-vinylpyrrolidinone.

In some embodiments, the monomer composition used to form the carbonyl-containing polymer can optionally include a hydrophobic monomer. As used herein, the term "hydrophobic monomer" refers monomers having a water miscibility (water in monomer) that is less than 1 weight percent. The hydrophobic monomers can be used in amounts that do not deleteriously affect the binding performance of the guanidinyl-containing monomer polymer and/or the water dispersibility of the guanidinyl-containing polymer. When present, the hydrophobic monomer is typically present in an amount in a range of 1 to 20 weight percent, 1 to 10 weight percent, or 1 to 5 weight percent based on a total weight of monomers in the monomer composition.

Useful classes of hydrophobic monomers include alkyl acrylate esters and amides, exemplified by straight-chain, cyclic, and branched-chain isomers of alkyl esters containing $C_1$-$C_{30}$ alkyl groups and mono- or dialkyl acrylamides containing $C_1$-$C_{30}$ alkyl groups. Useful specific examples of alkyl acrylate esters include: methyl acrylate, ethyl acrylate, n-propyl acrylate, n-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, lauryl acrylate, tridecyl acrylate, and tetradecyl acrylate. Useful specific examples of alkyl acrylamides include mono- and diacrylamides having pentyl, hexyl, heptyl, isobornyl, octyl, 2-ethylhexyl, iso-nonyl, decyl, undecyl, dodecyl, tridecyl, and tetradecyl groups may be used. The corresponding methacrylate esters may be used.

Additional useful classes of hydrophobic monomers further include vinyl monomers such as vinyl acetate, styrenes, and alkyl vinyl ethers, and maleic anhydride.

The monomer composition used to form the carbonyl-containing polymer is typically combined with a free radical initiator to form the polymerized product. Any suitable free radical initiator can be used. The initiator is typically present in an amount in the range of 0.01 to 5 weight percent, in the range of 0.01 to 2 weight percent, in the range of 0.01 to 1 weight percent, or in the range of 0.01 to 0.5 weight percent based on a total weight of monomers in the monomer composition.

In some embodiments, a thermal initiator can be used. Thermal initiators can be water-soluble or water-insoluble (i.e., oil-soluble) depending on the particular polymerization method used. Suitable water-soluble initiators include, but are not limited to, persulfates such as potassium persulfate, ammonium persulfate, sodium persulfate, and mixtures thereof an oxidation-reduction initiator such as the reaction product of a persulfate and a reducing agent such as a metabisulfite (e.g., sodium metabisulfite) or a bisulfate (e.g., sodium bisulfate); or 4,4'-azobis(4-cyanopentanoic acid) and its soluble salts (e.g., sodium or potassium). Suitable oil-soluble initiators include, but are not limited to, various azo compound such as those commercially available under the trade designation VAZO from DuPont (Wilmington, Del., USA) including VAZO 67, which is 2,2'-azobis(2-methylbutane nitrile), VAZO 64, which is 2,2'-azobis(isobutyronitrile), and VAZO 52, which is (2,2'-azobis(2,4-dimethylpentanenitrile); and various peroxides such as benzoyl peroxide, cyclohexane peroxide, lauroyl peroxide, and mixtures thereof.

In many embodiments, a photoinitiator can be used. Some illustrative photoinitiators are benzoin ethers (e.g., benzoin methyl ether or benzoin isopropyl ether) or substituted benzoin ethers (e.g., anisoin methyl ether). Other exemplary photoinitiators are substituted acetophenones such as 2,2-diethoxyacetophenone or 2,2-dimethoxy-2-phenylacetophenone (commercially available under the trade designation IRGACURE 651 from BASF Corp. (Florham Park, N.J., USA) or under the trade designation ESACURE KB-1 from Sartomer (Exton, Pa., USA)). Still other exemplary photoinitiators are substituted alpha-ketols such as 2-methyl-2-hydroxypropiophenone, aromatic sulfonyl chlorides such as 2-naphthalenesulfonyl chloride, and photoactive oximes such as 1-phenyl-1,2-propanedione-2-(0-ethoxycarbonyl) oxime. Other suitable photoinitiators include, for example, 1-hydroxycyclohexyl phenyl ketone (IRGACURE 184), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1 173).

The guanidinyl-containing polymers according to Formula (IV) are often the reaction product of a carbonyl-containing polymer precursor and a guanylating agent of Formula (VII).

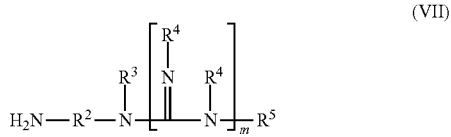

(VII)

In Formula (VII), the group $R^2$ is a covalent bond, $C_2$-$C_{12}$ (hetero)alkylene, or $C_5$-$C_{12}$ (hetero)arylene. Group $R^3$ is hydrogen, $C_1$-$C_{12}$ (hetero)alkyl, or $C_5$-$C_{12}$ (hetero)aryl. Each $R^4$ is independently hydrogen, $C_1$-$C_{12}$ (hetero)alkyl, or $C_5$-$C_{12}$ (hetero)aryl. Group $R^5$ is H, $C_1$-$C_{12}$ (hetero)alkyl, or $C_5$-$C_{12}$ (hetero)aryl, or —$N(R^4)_2$. The variable m is equal to 1 or 2.

For ease of description, the carbonyl-containing polymer can be represented by the formula Polymer-C(=O)—$R^1$. The carbonyl group can be in the backbone or in a pendant group but is usually in a pendant group. When reacted with a guanylating agent of Formula (VII), the carbonyl group in the carbonyl-containing polymer undergoes a condensation reaction with a terminal amine group of the guanylating agent. The guanidinyl-containing polymer typically has guanidinyl-containing pendant groups of Formula (VIII).

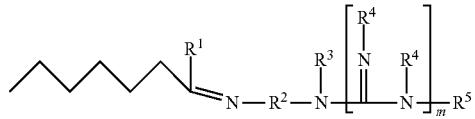

(VIII)

The groups $R^2$, $R^3$, $R^4$, and $R^5$ are the same as described above for Formula (VII). The group of formula

in Formula (VIII) is the linkage formed between the terminal amine of the ligand compound of Formula (VII) and the carbonyl group of the carbonyl-containing polymer. The wavy line denotes the attachment site of the group via a covalent bond to the rest of the polymer. Group $R^1$ is hydrogen (when the carbonyl group is an aldehyde group), $C_1$-$C_{12}$ (hetero)alkyl (when the carbonyl group is a ketone group and the ketone group is part of a pendant group), or $C_5$-$C_{12}$ (hetero)aryl (when the carbonyl group is a ketone group and the ketone group is part of a pendant group), or a residue of the polymer chain (when the carbonyl group is a group in the backbone of the carbonyl-containing polymer). In most embodiments, the group of Formula (VIII) is part of a pendant group of the guanidinyl-containing polymer.

In other embodiments, the guanidyl-containing polymer may be prepared in which the imine linking group (~~C($R^1$)=N—) is reduced to an amine linking group (~~CH($R^1$)—NH—). This may be effected by treating the extant ligand functional polymer with a reducing agent, such as sodium cyanoborohydride, or the reduction may be effected in situ by adding the reducing agent to the reaction mixture of the carbonyl functional (co)polymer and the compound of Formula V.

In many embodiments, some but not all of the carbonyl groups of the carbonyl-containing polymer are reacted with the guanylating agent of Formula (VII). Typically, at least 0.1 mole percent, at least 0.5 mole percent, at least 1 mole percent, at least 2 mole percent, at least 10 mole percent, at least 20 mole percent, or at least 50 mole percent of the carbonyl groups in the carbonyl-containing polymer precursor are reacted with the guanylating agent. Up to 100 mole percent, up to 90 mole percent, up to 80 mole percent, or up to 60 mole percent of the carbonyl groups can be reacted with the guanylating agent. For example, the guanylating agent can be used in amounts sufficient to functionalize 0.1 to 100 mole percent, 0.5 to 100 mole percent, 1 to 90 mole percent, 1 to 80 mole percent, 1 to 60 mole percent, 2 to 50 mole percent, 2 to 25 mole percent, or 2 to 10 mole percent of the carbonyl groups in the carbonyl-containing polymer.

The guanidinyl-containing polymer can be crosslinked. In some embodiments, the carbonyl-containing polymer is crosslinked prior to reaction with the guanylating agent. The carbonyl-containing polymer can be crosslinked either by addition of a crosslinking monomer in the monomer composition used to form the carbonyl-containing polymer or by reaction of some of the carbonyl groups of the previously formed carbonyl-containing polymer with a suitable crosslinking agent. In other embodiments, crosslinking can occur after reaction of the carbonyl-containing polymer with the guanylating agent. In this embodiment, crosslinking can occur by reaction of some of the remaining carbonyl groups (those carbonyl groups in the carbonyl-containing polymer precursor that were not reacted in the process of forming the guanidinyl-containing polymer) with a suitable crosslinking agent or by reaction of some of the guanidinyl groups with a crosslinking agent.

Suitable crosslinking monomers for use in the monomer composition to form the carbonyl-containing polymer include, but are not limited to, N,N'-(hetero)alkylenebis (meth)acrylamide. These crosslinking monomers have at least two (meth)acryloyl groups that can react to crosslink one polymeric chain with another polymeric chain or that can react to crosslink one part of a polymeric chain with another part of the same polymeric chain. Suitable N,N'-alkylenebis(meth)acrylamide crosslinking monomers include, but are not limited to, those having an alkylene group with 1 to 10, 1 to 8, 1 to 6, or 1 to 4 carbon atoms such as N,N'-methylenebisacrylamide, N,N'-methylenebismethacrylamide, N,N'-ethylenebisacrylamide, N,N'-ethylenebismethacrylamide, N,N'-propylenebisacrylamide, N,N'-propylenebismethacrylamide, N,N'-hexamethylenebisacrylamide, and N,N'-hexamethylenebismethacrylamide. Suitable N,N'-heteroalkylenebis(meth)acrylamide crosslinking monomers include, but are not limited to, N,N'-cystaminebisacrylamide, N,N'-piperazinebisacrylamide, and N,N'-piperazinebismethacrylamide. These crosslinking monomers are commercially available from various suppliers such as Sigma-Aldrich (Milwaukee, Wis.) and Polysciences, Inc. (Warrington, Pa.). Alternatively, these crosslinking monomers can be synthesized by procedures described in the art such as, for example, in Rasmussen, et al., Reactive Polymers, 16, 199-212 (1991/1992).

Suitable crosslinkers for reaction with carbonyl groups of the carbonyl-containing polymer precursor or remaining carbonyl groups of the guanidinyl-containing polymer include molecules comprising two or more amine, hydrazine, hydrazide, or O-substituted hydroxylamine moieties. Specific examples of polyamine (compounds with two or more amine groups) crosslinkers include 1,2-ethanediamine, 1,2-propanediamine, 1,3-propanediamine, 1,6-hexanediamine, tris-(2-aminoethyl)amine, diethylenetriamine, triethylenetetraamine, tetraethylenepentaamine, N,N'-bis(3-aminopropyl)piperazine, N-(2-aminoethyl)piperazine, polyethyleneimine, polyallylamine, and the like. Specific examples of polyhydrazines (compounds with two or more hydrazine groups) include 1,1'-ethylenebishydrazine, 1,1'-propylenebishydrazine, 1,1'-ethylenebis(1-cyclohexylhydrazine), 1,1'-decamethylenebis(1-n-butylhydrazine), and the like. Specific examples of useful polyhydrazides (compounds with two or more hydrazide groups) include succinic dihydrazide, adipic dihydrazide, terephthalic dihydrazide, 1,3-diaminoguanidine, and the like. Specific examples of polyhydroxylamines (compounds with two or more O-substituted hydroxylamine groups) include O,O'-ethylenebishydroxylamine (1,2-bisaminoxy ethane), 1,6-bisaminoxyhexane, and the like. Alternatively, crosslinkers comprising two or more different moieties selected from amine, hydrazine, hydrazide, or O-substituted hydroxylamine moieties can be used.

Suitable crosslinkers for reaction with the guanidinyl groups of the guanidinyl-containing polymer include amine-reactive compounds such as bis- and polyaldehydes such as glutaraldehyde, bis- and polyepoxides such as butanedioldiglycidylether and ethyleneglycoldiglycidylether, polycarboxylic acids and their derivatives (e.g., acid chlorides), polyisocyanates, formaldehyde-based crosslinkers such as hydroxymethyl and alkoxymethyl functional crosslinkers, such as those derived from urea or melamine.

Rather than reacting a precursor polymer with a guanylating agent to prepare a guanidinyl-containing polymer, the guanidinyl-containing polymer can be prepared by free radical polymerization of a guanidinyl-containing monomer, which refers to a monomer having an ethylenically unsaturated group and a guanidinyl-containing group. Example guanidinyl-containing monomers are of Formula (IX) and (X).

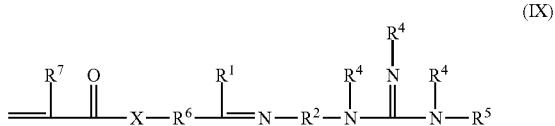
(IX)

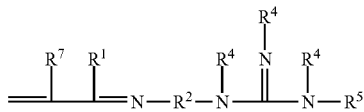
(X)

In Formulas (IX) and (X), group $R^1$ is hydrogen, $C_1$-$C_{12}$ alkyl, or $C_5$-$C_{12}$ (hetero)aryl. Group $R^2$ is a covalent bond, a $C_2$ to $C_{12}$ alkylene, a $C_5$-$C_{12}$ (hetero)arylene, a divalent group of formula

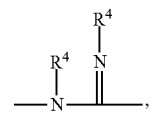, or a divalent group of formula

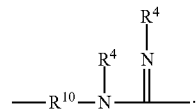.

Group $R^{10}$ is $C_2$ to $C_{12}$ alkylene, or $C_5$-$C_{12}$ (hetero)arylene. Each $R^3$ is independently hydrogen, hydroxyl, $C_1$-$C_{12}$ alkyl, or $C_5$-$C_{12}$ (hetero)aryl. $R^3$ is preferably hydrogen or $C_1$-$C_4$ alkyl. Group $R^4$ is hydrogen, $C_1$-$C_{12}$ alkyl, $C_5$-$C_{12}$ (hetero)aryl, or —N($R^3$)$_2$. Preferably, $R^4$ is hydrogen or $C_1$-$C_4$ alkyl. Group X is oxy or —NR$^3$—. Group $R^6$ is a $C_2$ to $C_{12}$ alkylene. Group $R^7$ is hydrogen or $CH_3$.

The monomers of Formula (IX) and (X) can be formed, for example, by a condensation reaction of a carbonyl-containing monomer with the guanylating agent of Formula (VII). Example carbonyl-containing monomers include, but are not limited to, acrolein, vinyl methyl ketone, vinyl ethyl ketone, vinyl isobutyl ketone, isopropenyl methyl ketone, vinyl phenyl ketone, diacetone (meth)acrylamide, acetonyl acrylate, and acetoacetoxyethyl (meth)acrylate.

The monomers of Formula (IX) or (X) may be reacted to form homopolymers or can be copolymerized with other ethylenically unsaturated monomers such as any of the hydrophilic monomers described above. A free radical initiator such as those described above in the preparation of the carbonyl-containing polymer can be used. This reaction is further described in International Patent Publication WO 2011/103106 A1 (Rasmussen et al.).

Guanidinyl-containing polymers formed from a monomer of Formula (X) or (XI) are typically crosslinked by addition of a crosslinking monomer to the monomer composition. Suitable crosslinking monomers include N,N-alkylenebis (meth)acrylamide, N,N'-heteroalkylenebis(meth)acrylamide, or a combination thereof. More specific crosslinkers are the same as described above for use in a monomer composition for preparation of the carbonyl-containing polymers. Alternatively, the guanidinyl-containing polymers can be formed without a crosslinking monomer and the guanidinyl groups can be reacted with crosslinkers as described above.

The guanidinyl-containing polymer can be bound to the substrate using any suitable method or means. In some embodiments, the guanidinyl-containing polymer is grafted (i.e., covalently attached) to the substrate. In other embodiments, the guanidinyl-containing polymer is contacted with the substrate prior to crosslinking and is crosslinked in the presence of the substrate. When the substrate includes fibers (e.g., the substrate includes a woven or nonwoven fabric), the crosslinked guanidinyl-containing polymer can surround fibers. The fibers and the crosslinked guanidinyl-containing polymers can be so intermingled that separation is not possible by a technique such as peeling or dissolution or by any other technique without the destruction of the wipe.

The cationic coating composition that includes the guanidinyl-containing polymer is applied to the substrate. Coating methods include the techniques commonly known such as dip, spray, knife, bar, slot, slide, die, roll, and gravure coating. The cationic coating can be disposed on a surface of the substrate or distributed throughout the substrate. For example, the cationic coating composition can be applied to the surface of the substrate. Depending on the porosity of the substrate, the viscosity of the cationic coating composition, and the relative volume of the cationic coating composition to that of the substrate, at least some of the cationic coating composition can permeate into the substrate. In some examples, the cationic coating can be poured over the substrate such that the substrate is immersed in or covered with the cationic coating composition. The cationic coating composition often includes a liquid such as water, an organic solvent such as a polar organic solvent (e.g., a polar that is miscible with water), or a mixture thereof. The cationic coating composition can additionally include the crosslinking agent for the guanidinyl-containing polymer. Depending on the chemistry used to bind the gaunidinyl-containing polymer to the substrate, a compound for grafting or attaching the guanidinyl-containing polymer to the substrate can be included in the cationic coating composition. After application to the substrate, the cationic coating composition can be dried to remove the liquid or any desired portion of the liquid. In some embodiments, the drying to remove the liquid is accomplished through evaporation.

In some embodiments, the cationic coating composition is applied to the substrate by first applying the precursor polymer for the guanidinyl-containing polymer followed by application of the guanylating agent. For example, an amino-containing polymer precursor or a carbonyl-containing polymer precursor can be applied to the substrate in a first coating composition. A second coating composition can then be applied that includes the guanylating agent. The crosslinking agent can be added in the first coating composition with the precursor polymer, in the second coating composition with the guanylating agent, or in a third coating composition. Any of the coating compositions can include an optional compound for grafting the guanidinyl-containing polymer to the substrate.

In other embodiments, the guanidinyl-containing polymer is applied to the substrate. The coating composition that contains the guanidinyl-containing polymer can further include a crosslinking agent, an optional grafting compound, or a mixture thereof. Alternatively, the crosslinking agent and/or optional grafting agent can be added in a second coating composition.

Some substrates have amine-reactive functional groups such as halide groups, epoxy groups, ester groups, or isocyanate groups. These amine-reactive groups can react with amino groups of the guanidinyl-containing polymer. The amino groups can be part of the guanidinyl group (such as a terminal amino group) or any other amino groups that are present in the guanidinyl-containing polymer. For example, if the guanidinyl-containing polymer was formed from an amino-containing polymer precursor, there can be amino groups in the backbone of the guanidinyl-containing polymer.

The amine-reactive functional groups on the substrate may be part of the polymeric material used to form the substrate or may be provided by any of the techniques known to one in the art. In one embodiment, the substrate may have a primer layer containing a polymer having amine-reactive functional groups. That is, the substrate includes a base polymer layer and a primer layer. Especially useful polymers of use in the primer layer are azlactone functional polymers such as those described in U.S. Pat. No. 7,101,621 (Haddad et al.). Such primer layer coatings are typically hydrophilic and are compatible with the cationic coating composition. Useful coating techniques for the primer layer include applying a solution or dispersion of the polymer having amine-reactive functional groups, optionally further including a crosslinker, onto the substrate. Coating methods include the techniques commonly known such as dip, spray, knife, bar, slot, slide, die, roll, and gravure coating. The application step is generally followed by evaporating the solvent to form the polymer coating.

In some embodiments, the polymer having amine-reactive functional groups may be grafted to the surface of a substrate by ionizing radiation-initiated graft polymerization of a monomer having a free-radically polymerizable group and a second functional group reactive with the guanidinyl-containing polymer. One such polymer having an amine-reactive functional group is described U.S. Pat. No. 8,551,894 (Seshadri et al.). Suitable monomers include, for example, an azlactone-functional monomer, isocyanatoethyl (meth) acrylate, and a glycidyl (meth)acrylate. Other suitable monomers include, for example, those having a carbonyl group as described in U.S. Pat. No. 8,377,672 (Rasmussen et al.). The monomers can graft (i.e., form a covalent bond) to the surface of the substrate when exposed to an ionizing radiation, preferably e-beam or gamma radiation. That is, reaction of an ethylenically unsaturated group (e.g., a (meth) acryloyl group) of the monomer with the surface of the substrate in the presence of the ionizing radiation results in grafting to the substrate via the ethylenically unsaturated group.

Some substrates have carbonyl-reactive groups such as amines. These carbonyl-reactive groups can react with a carbonyl-containing polymer precursor prior to reaction with the guanylating agent or can react with any residual carbonyl groups in the guanidinyl-containing polymer after reaction with the guanylating agent.

The carbonyl-reactive functional groups on the substrate may be part of the polymeric material used to form the substrate or may be provided by any of the techniques known to one in the art. In some embodiments, the carbonyl-reactive groups can be grafted to the surface of a substrate by ionizing radiation-initiated graft polymerization of a monomer having a free-radically polymerizable group and a second group capable of reacting with a carbonyl group of either the carbonyl-containing precursor or any residual carbonyl groups in the guanidinyl-containing polymer after reaction with a guanylating agent. Such monomers are various amino-containing monomers such as those of Formula (V) where $R^8$ is hydrogen.

In another method of bonding the guanidinyl-containing polymer to the substrate, a compound such as benzophenone or acetophenone can be added to the monomer composition used to form the carbonyl-containing precursor. Upon exposure to UV radiation, the benzophenone or acetophenone can abstract a hydrogen atom from the polymeric material of the substrate. This abstraction results in the formation of a free radical site on the polymeric material of the substrate. The monomers then interact with the free radical site and become graft polymerized onto the substrate. The covalently attached carbonyl-containing polymer can then be treated with a guanylating agent to form the guanidinyl-containing polymer.

The bonding of the guanidinyl-containing polymer to the substrate provides enhanced affinity for various microorganisms while retaining many of the desirable features of the substrate such as mechanical stability, thermal stability, porosity, and flexibility. The wipes typically contain an amount of the bound guanidinyl-containing polymer in a range of 0.1 to 10 weight percent, in a range of 0.1 weight percent to 5 weight percent, in a range of 0.1 to 3 weight percent, in a range of 0.1 to 2, or in a range of 0.1 weight percent to 1 weight percent, based on a total weight of the wipe.

Further details related to guanidinyl containing polymers can be found, for example in WO 2011/103106, WO 2011/109151, WO 2014/204763, and WO 2014/209798, the disclosures of which are incorporated herein by reference thereto.

Optional Components in First, Second, or Both Compositions

Disclosed compositions (first, second or both) can also include one or more other optional components. For example surfactants including anionic surfactants, amphoteric surfactants, nonionic surfactants or combinations thereof may be included in disclosed compositions. Surfactants, if utilized, may be used to stabilize the dispersed particles in the composition for example. In some embodiments, anionic surfactants or nonionic surfactants can optionally be utilized in disclosed compositions.

Anionic surfactants can include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, alkyl and aralkyl glycerylether sulfonates, alkyl and aralkyl sulfosuccinates, alkylglyceryl ether sulfonates, alkyl phosphates, aralkyl phosphates, alkylphosphonates, and aralkylphosphonates. These anionic surfactants may have a metal or organic ammonium counterion. In some embodiments anionic surfactants selected from sulfonates and sulfates, and phosphonates and phosphates may be utilized in disclosed compositions.

Suitable anionic surfactants can include sulfonates and sulfates such as alkyl sulfates, alkylether sulfates, alkyl sulfonates, alkylether sulfonates, alkylbenzene sufonates, alkylbenzene ether sulfates, alkylsulfoacetates, secondary alkane sulfonates, secondary alkylsulfates, and the like. Many of these can be represented by the formulas: $R^{14}$—$(OCH_2CH_2)n(OCH(CH_3)CH_2)_p$-$(Ph)_a$-$(OCH_2CH_2)_m$—$(O)_b$—$SO_3$-M+ and $R^{14}$—$CH[SO_3$-M+]—$R^{15}$ wherein: a and b=0 or 1; n, p, and m=0-100 (in some embodiments 0-20, and in some embodiments 0-10); $R^{14}$ and $R^{15}$ are $(C_1$-$C_{12})$ alkyl group (saturated straight, branched, or cyclic group) that may be optionally substituted by N, O, or S atoms or hydroxyl, carboxyl, amide, or amine groups provided at least one $R^H$ or $R^{15}$ is at least $C_8$; Ph=phenylene; and M is a cationic counterion such as H, Na, K, Li, ammonium, or a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. In some embodiments for this class, $R^{14}$ can include an alkylamide group such as $R^{16}$—$C(O)N(CH_3)CH_2CH_2$— as well as ester groups such as —$OC(O)$—$CH_2$— wherein $R^{16}$ is a $(C_5$-$C_{22})$ alkyl group (branched, straight, or cyclic group). Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a sodium salt of a secondary alkane sulfonate.

Examples can include, for example $(C_{14}$-$C_{17})$secondary alkane sulfonates (alpha-olefin sulfonates) available from Clariant Corp., Charlotte, N.C.; methyl-2-sulfoalkyl esters such as sodium methyl-2-sulfo($C_{12-16}$)ester and disodium 2-sulfo($C_{12}$-$C_{16}$)fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company; dialkylsulfosuccinates such as dioctylsodiumsulfosuccinate available as Aerosol OT from Cytec Industries.

Suitable anionic surfactants can also include phosphates such as alkyl phosphates, alkylether phosphates, aralkylphosphates, and aralkylether phosphates. Many may be represented by the formula:

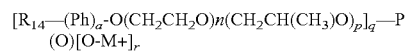

[$R_{14}$—(Ph)$_a$-$O(CH_2CH_2O)n(CH_2CH(CH_3)O)_p]_q$—P(O)[O-M+]$_r$ wherein: Ph, $R_{14}$, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement. Examples can include a mixture of mono-, di- and tri-(alkylalkoxylate)-o-phosphoric acid esters such as trilaureth-4-phosphate commercially available under the trade designation HOSTAPHAT 340KX from Clariant Corp., as well as PPG-5 ceteth 10 phosphate available under the trade designation CRODAPHOS SG from Croda Inc., Parsippany, N.J., and mixtures thereof. Trade names for anionic surfactants include Rhodocal DS-10, Stepan Mild, and Complexmix.

Amphoteric Surfactants. Surfactants of the amphoteric type include surfactants having tertiary amine groups, which may be protonated, as well as quaternary amine containing zwitterionic surfactants. In some embodiments ammonium carboxylates and ammonium sulfonates may be utilized.

The ammonium carboxylate class of surfactants can be represented by the following formula: $R^{17}$—$C(O)$—$NH)a$-$R^{18}$—$N+(R^{19})_2$—$R^{20}$—$COO$— wherein: a=0 or 1; $R^{17}$ is a $(C_7$-$C_{21})$alkyl group (saturated straight, branched, or cyclic group), a $(C_6$-$C_{22})$aryl group, or a $(C_6$-$C_{22})$aralkyl or alkaryl group (saturated straight, branched, or cyclic alkyl group), wherein $R^{17}$ may be optionally substituted with one or more N, O, or S atoms, or one or more hydroxyl, carboxyl, amide, or amine groups; $R^{19}$ is H or a $(C_1$-$C_8)$alkyl group (saturated straight, branched, or cyclic group), wherein $R^{19}$ may be optionally substituted with one or more N, O, or S atoms, or one or more hydroxyl, carboxyl, amine groups, a $(C_6$-$C_9)$aryl group, or a $(C_6$-$C_9)$aralkyl or alkaryl group; and $R^{18}$ and $R^{20}$ are each independently a $(C_1$-$C_{10})$alkylene group that may be the same or different and may be optionally substituted with one or more N, O, or S atoms, or one or more hydroxyl or amine groups. In some embodiments, in the formula above, $R^{17}$ is a $(C_1-C_{18})$alkyl group, $R^{19}$ is a $(C_1-C_2)$alkyl group which can be substituted with a methyl or benzyl group and in some embodiments with a methyl group. When $R^{19}$ is H it is understood that the surfactant at higher pH values could exist as a tertiary amine with a cationic counterion such as Na, K, Li, or a quaternary amine group. Examples of such amphoteric surfactants include, but are not limited to: certain betaines such as cocobetaine and cocamidopropyl betaine (commercially available under the trade designations MACKAM CB-35 and MACKAM L from Mclntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM IL, MACKAM 2L, and MACKAM 15 IL, respectively, from Mclntyre Group Ltd.).

The ammonium sulfonate class of amphoteric surfactants are often referred to as "sultaines" or "sulfobetaines" and can be represented by the following formula: $R^{17}$—C(O)—NH)$_a$—$R^{18}$—N$^+$($R^{19}$)$_2$—$R^{20}$—SO$_3^-$ wherein $R^{17}$—$R^{20}$ and "a" are defined above. Examples include cocamidopropyl-hydroxysultaine (commercially available as MACKAM 50-SB from Mclntyre Group Ltd.). The sulfoamphoterics may be utilized instead of the carboxylate amphoterics in some embodiments since the sulfonate group will remain ionized at much lower pH values.

Nonionic Surfactants. Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON X-100 and nonyl phenoxy poly(ethyleneoxy) ethanol available under the trade name NONIDET P-40, both from Sigma, St. Louis, Mo.), ethoxylated and/or propoxylated aliphatic alcohols (e.g., that available under the trade name Brij from ICI), ethoxylated glycerides, ethoxylated/propoxylated block copolymers such as the Pluronic and Tetronic surfactants available from BASF, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD-FS 300 from 3M Company, St. Paul, Minn., and ZONYL from Dupont de Nemours Co., Wilmington, Del.), and polymerizable (reactive) surfactants (e.g., SAM 211 (alkylene polyalkoxy sulfate) surfactant available under the trade name MAZON from PPG Industries, Inc., Pittsburgh, Pa.). In some embodiments, the nonionic surfactants useful in the compositions can be selected from the group consisting of Poloxamers such as PLURONIC from BASF, sorbitan fatty acid esters like TWEEN, and mixtures thereof.

Disclosed compositions can also include other optional components. One such optional component includes antimicrobial components. Cationic quaternary ammonium salts (some of which are antimicrobial agents) including, but are not limited to cetyl pyridinium chloride, cetrimonium bromide (CTAB), behentrimonium chloride, bis-biguanides include chlorhexidine salts and polymeric guanides such as polyhexamethylenebiguanide (PHMB), benzethonium chloride, chlorhexidine salts such as chlorhexidine gluconate, octenidine salts such as octenidine dihydrochloride, stearalkonium chloride etc. and mixtures thereof can be used. The antimicrobials, if present can generally be present from 0.01-1 wt % based on the total weight of the composition. Non-ionic antimicrobials such as triclosan can also be used. Cationic compounds can be used in relatively small concentrations, as long as the stability of the composition is not compromised.

Amine compounds can also optionally be added to disclosed compositions. Amine compounds may be added in order to bind to the acrylate copolymer particles, i.e. to help with neutralization of the polymer while also interacting with the surface of the spores. These can include, for example ethoxylated amines such as Jeffamines, and peg 8 oleyl amine.

Humectants can also optionally be added to disclosed compositions. Suitable humectants may include for example glycerin, propylene glycol, sorbitol, polypropylene glycol, polyethylene glycol, and combinations thereof.

Skin conditioning agents including emollients and polymers can also optionally be added to disclosed compositions. Useful skin conditioning agents such as mono-, di- and tri-glycerides, castor oil, allantoin, lanolin and its derivatives, cetyl alcohol and cationic polymers could be utilized for example. Emollients may be selected from those in U.S. Pat. No. 5,951,993 which is incorporated herein by reference, for example.

Thickeners can also optionally be added to disclosed compositions. In some embodiments, the thickeners could be organic thickeners. Suitable organic thickeners can include for example guar gum, hydroxyethyl cellulose, hydroxyl propyl cellulose, hydroxybutyl cellulose, hydroxypropyl methyl cellulose, polyvinylpyrrolidinone, as well as those disclosed in U.S. Pat. No. 8,062,649, incorporated herein by reference, which are used in the amount typically ranging from 0.1-2 wt % based on the total weight of the composition. Inorganic thickeners such as hydrated silica may be used in the amount of about 0.5-10 wt % or greater based on the total weigh of the composition.

Abrasive or mechanical exfoliating agents could also optionally be included in disclosed compositions. In some embodiments abrasive or exfoliating materials could include water insoluble abrasives such as phosphates, carbonates, silicates, hydrated silica, hydrated alumina, bentonite, as well as polymeric beads such a poly methyl methacrylate (PMMA), polystyrene, and polyolefin beads and particulates and the like as well as mixtures thereof. In some cases, other mild exfoliating agents could optionally be used in disclosed compositions for mechanically removing spores. Illustrative exfoliating agents could include arrowroot powder or walnut powder for example.

Methods and Illustrative Steps Thereof

Disclosed methods can be utilized on virtually any surface including for example skin, medical equipment, surfaces in a medical environment, or any combinations thereof. In some embodiments, disclosed methods can be utilized on skin of patients, health care workers, other individuals, or any combination thereof. Both the first and the second compositions are liquids.

The surface on which the spores are located and are to be dislodged from can be contacted with a first composition by applying or bringing the first composition to the surface, by bringing the surface into contact with the first composition, or by combinations thereof. More specifically, the first composition and the surface can be brought into contact by spraying the first composition onto the surface, by dispensing the first composition onto the surface, by dipping the surface into the first composition, by pouring the first composition onto the surface, or by any combination thereof.

In some embodiments bringing the surface into contact with the first composition can be accomplished by dispensing the first composition into or onto an article. Dispensing can be accomplished via pouring, spraying, bringing the article into the first composition (e.g., dipping), or submerging the article in the first composition, for example. As indicated, the first composition can be dispensed into or onto an article.

In embodiments where the first composition is dispensed into an article, illustrative articles can include for example basins, bowls, and tubs. Such methods can be useful in instances where the skin from which the spores are to be removed is to be brought into contact with the first composition in the article, for example. More specifically, this can be useful if some part of, or all of the patient is going to be immersed in the first composition in the article. For example, the patient could be going to bathe in the article (e.g., a tub). Another example could include a basin where some part of a patient, for example one or more hands are to be immersed in the first composition in the basin. This can also be useful if a secondary article is going to be immersed in the first composition in the article and then that secondary article is going to be brought into contact with the skin.

The amount of the first composition dispensed into an article, or an effective amount, can depend at least in part on how the skin from which the spores are to be removed is to be brought into contact with the first composition in the article, the particular skin to be cleaned, the type of optional mechanical action (discussed below), whether or not there is a secondary article, or combinations thereof.

In some embodiments where the first composition is to be dispensed into an article, not less than 5 milliliters (mL) of the first composition can be dispensed into an article, not less than 10 mL of the first composition, not less than 20 mL of the first composition, or not less than 50 mL of the first composition. Relevant upper amounts of the first composition would depend at least in part on the particular article (e.g., its maximum volume), the volume to be immersed (if immersion is relevant) in the article, or combinations thereof.

In some embodiments where the composition is to be dispensed into an article, the amount dispensed, or an effective amount can also depend, at least in part, on the surface area, for example surface area of skin from which spores are to be removed. In some embodiments, not less than 1 mL of the first composition/10 $cm^2$ of skin surface from which spores are to be removed can be dispensed into the article, and in some embodiments not less than 1 mL of the first composition/50 $cm^2$ of skin surface from which spores are to be removed can be dispensed into the article.

In some embodiments, the step of contacting the surface with the first composition can include contacting the surface with an article that has been previously contacted with the first composition. For example, an article could be contacted with or treated with the composition and then that treated article could be contacted with the surface.

In some embodiments where the first composition is dispensed onto an article, illustrative articles can include for example wipes, sponges, cloths, loofahs, brushes, pads, or fibrous mats for example. The second composition is also (also when the first composition is also optionally dispensed onto an article) dispensed onto an article and discussion related to such articles (which contain the first composition or the second composition, or both in separate articles) can apply to the first composition or articles associated therewith, the second composition or articles associated therewith or both.

It should be understood that dispensing a composition onto an article can imply bringing the composition to the article, bringing the article to the composition, or any combination thereof. Such methods can be useful in instances where the skin from which the spores are to be removed is to be brought into contact with an article that is associated with the composition, for example. More specifically, this can be useful for wiping affected skin of a patient with the article to which the composition has been dispensed, to remove spores from the skin of the patient. In some embodiments the composition can be dispensed onto a wipe with a coating, for example a cationic coating.

The amount of the composition dispensed onto an article, or an effective amount, can depend at least in part on the particular surface to be cleaned (e.g., skin), the total surface area of the surface (e.g., skin) to be cleaned, the type of optional mechanical action (discussed below), the particular type of article (e.g., the amount the article can absorb, hold, etc.) or combinations thereof.

In some embodiments where the composition is to be dispensed onto an article, not less than 30 mL of the composition can be dispensed onto an article, not less than 40 mL of the composition, not less than 50 mL of the composition, or not less than 20 mL of the composition. Relevant upper amounts of the composition would depend at least in part on the particular article (e.g., its surface area, the material thereof, its porosity, etc.), a desired level of "wetness" of the article, and combinations thereof.

In some embodiments where the composition is to be dispensed onto an article, the amount dispensed, or an effective amount can also depend, at least in part, on the surface area of skin from which spores are to be removed. In some embodiments, not less than 1 mL of the composition/10 $cm^2$ of skin surface from which spores are to be removed can be dispensed onto the article, and in some embodiments not less than 5 mL of the composition/10 $cm^2$ of skin surface from which spores are to be removed can be dispensed onto the article.

In some embodiments where the composition is to be dispensed onto an article, an effective amount is one which provides a sufficient amount of the composition in contact with the skin surface from which spores are to be removed. In some embodiments, an effective amount can be described with respect to the amount of the composition necessary to saturate the article.

In some embodiments, an effective amount of the composition that can be dispensed onto an article can be an amount that renders the wipe (for example) as wet as possible so that the saturation amount is bypassed. In some embodiments, it may not be desirable to go below the saturation level, or not less than 5% below the saturation amount. In some embodiments, an effective amount of the composition that can be dispensed onto an article can be not greater than 40% above the saturation amount of the article. In some embodiments, an effective amount can be not greater than 20% above the saturation amount of the article, in some embodiments not greater than 15% above the saturation amount, and in some embodiments not greater than 5% above the saturation amount. In some embodiments, an effective amount of a composition can be one that makes the article as wet as possible while maintaining a useful article.

For the purposes of illustration only, a 4 inch×6 inch SONTARA® 8005, 100% PET (DuPont) wipe has a saturation amount of 3.5 g liquid, so illustrative effective amounts for such an article could include not greater than 4.9 g of liquid, not greater than 4.2 g liquid, not greater than 4.0 g liquid, not greater than 3.7 g liquid, and not less than 3.3 g liquid.

In some embodiments where the composition is dispensed onto an article, a different first step can be utilized. For example, in some embodiments, a first step in disclosed methods can include obtaining an article containing a composition. An article containing a composition is an article that is capable of carrying an effective amount of a composition distributed throughout the material of the article.

The step of obtaining an article containing a composition can be accomplished by contacting a carrier with a composition, such as those compositions described above. This step can be carried out as discussed above with respect to dispensing the composition onto an article, which in this case is the carrier. The carrier can be a wipe, or a sponge for example. Also as discussed above, the carrier can be dipped into the composition, the composition can be sprayed onto the carrier, the composition can be applied to the carrier, or any combination thereof.

The step of obtaining an article containing a composition can also alternatively be accomplished by obtaining a carrier pre-moistened with the composition. For example, one or more articles containing a composition can be packaged together in any type of air tight or re-sealable packaging, for example a foil pack, a plastic container, or any combination thereof.

Some disclosed methods include a step of subjecting the surface contacted with the composition to mechanical action. This can include the first composition, the second composition, or both. Virtually any type of mechanical action could be utilized in disclosed methods. Illustrative types of mechanical action can include, for example, rubbing the surface with some article (for example an article treated with the composition, or an article not treated with the first composition), moving or scraping an article across the surface, moving a surface contacted with the composition across another surface contacted with the composition, or any combination thereof. In some embodiments, mechanical action can include rubbing, wiping, scraping, or scouring the surface with the article treated with the composition. In some embodiments, mechanical action can include moving a first surface contacted with the composition across or over a second surface contacted with the composition. A specific example of such an embodiment can include rubbing two hands contacted with the composition together.

The step of subjecting the surface to mechanical action can occur for any amount of time. In some embodiments, the surface can be subjected to mechanical action for not less than 5 seconds, not less than 10 seconds, or not less than 20 seconds. In some embodiments, the surface can be subjected to mechanical action for not greater than 2 minutes, or not greater than 1 minute, for example.

In some embodiments, the steps of contacting the surface with a first composition and optionally subjecting the surface in contact with the first composition to mechanical action can occur with at least some overlap. For example, in some embodiments, while at least some of the first composition is being contacted with the surface, mechanical action can begin. Specifically, for example, while a hand, or hands, is being dipped into the first composition (or even soaked in the first composition), the hands can be rubbed together. Either (or both) of the steps of contacting the surface with the first composition or subjecting the surface to mechanical action can be repeated more than once in some embodiments.

In some embodiments, the step of subjecting the skin to mechanical action can be described by the force of the mechanical action. In some embodiments, the mechanical action on the skin can have a force of not less than 20 N.

In some embodiments where the second composition is dispensed onto an article, an additional step can be utilized. For example, in some embodiments, a step in disclosed methods can include obtaining a cationic coated article containing a second composition. A cationic coated article containing a second composition is a cationic coated article that is capable of carrying, carries, or both an effective amount of a second composition distributed throughout the material of the article.

The step of obtaining a cationic coated article containing a second composition can be accomplished by contacting a cationic coated carrier with a second composition, such as those compositions described above. This step can be carried out as discussed above with respect to dispensing the second composition onto a cationic coated article, which in this case is the carrier. The carrier can be a wipe, or a sponge for example that is coated with a disclosed cationic coating. Also as discussed above, the carrier can be dipped into the second composition, the second composition can be sprayed onto the carrier, the second composition can be applied to the carrier, or any combination thereof.

The amount of the second composition dispensed onto the cationic coated article, or an effective amount, can depend at least in part on the particular surface to be cleaned (e.g., skin), the total surface area of the surface (e.g., skin) to be cleaned, the type of optional mechanical action (discussed below), the particular type of cationic coated article (e.g., the amount the article can absorb, hold, etc. because of size or chemical components) or combinations thereof.

In some embodiments where the second composition is to be dispensed onto an article, not less than 3 mL of the second composition can be dispensed onto an article, not less than 4 mL of the second composition, not less than 5 mL of the second composition, or not less than 2 mL of the second composition. Relevant upper amounts of the second composition would depend at least in part on the particular article (e.g., its surface area, the material thereof, its porosity, etc.), a desired level of "wetness" of the article, and combinations thereof.

In some embodiments where the second composition is to be dispensed onto a cationic coated article, the amount dispensed, or an effective amount can also depend, at least in part, on the surface area of skin from which spores are to be removed. In some embodiments, not less than 1 mL of the second composition/10 $cm^2$ of skin surface from which spores are to be removed can be dispensed onto the cationic coated article, and in some embodiments not less than 5 mL of the second composition/10 $cm^2$ of skin surface from which spores are to be removed can be dispensed onto the cationic coated article.

In some embodiments where the second composition is to be dispensed onto a cationic coated article, an effective amount is one which provides a sufficient amount of the second composition in contact with the skin surface from which spores are to be removed. In some embodiments, an effective amount can be described with respect to the amount of the second composition necessary to saturate the cationic coated article. An article is "saturated" when the article is contacted with more of the second composition than the article can hold and reasonable pressure is applied to the article to remove the excess. In articles that are easily wet, "saturation" can be determined substantially immediately after incorporation. In articles that are more hydrophobic, it may be necessary to expose the article to the second composition for a longer period of time. A reasonable amount of pressure can be that applied with an average hand squeezing motion until no further solution is seen dripping from the wipe. The amount of the second composition retained in the article after pressure has been applied can be referred to as the saturation amount.

In some embodiments, an effective amount of the second composition that can be dispensed onto a cationic coated article can be an amount that renders the wipe (for example) as wet as possible so that the saturation amount is bypassed. In some embodiments, it may not be desirable to go below the saturation level, or not less than 5% below the saturation amount. In some embodiments, an effective amount of the second composition that can be dispensed onto an article can be not greater than 40% above the saturation amount of the article. In some embodiments, an effective amount can be not greater than 20% above the saturation amount of the article, in some embodiments not greater than 15% above the saturation amount, and in some embodiments not greater than 5% above the saturation amount. In some embodiments, an effective amount of a second composition can be one that makes the article as wet as possible while maintaining a useful article.

For the purposes of illustration only, a 4 inch×6 inch SONTARA® 8005, 100% PET (DuPont) wipe has a saturation amount of 3.5 g liquid, so illustrative effective amounts for such an article could include not greater than 4.9 g of liquid, not greater than 4.2 g liquid, not greater than 4.0 g liquid, not greater than 3.7 g liquid, and not less than 3.3 g liquid.

The step of obtaining a cationic coated article containing a second composition can also alternatively be accomplished by obtaining a cationic coated carrier pre-moistened with the second composition. For example, one or more cationic coated articles containing a second composition can be packaged together in any type of air tight or re-sealable packaging, for example a foil pack, a plastic container, or any combination thereof.

In some embodiments, disclosed methods can include a first step of contacting a first composition with a surface and a second step of contacting the surface with a cationic coated wipe and a second composition. In some embodiments, the first composition can include greater than 60 wt % of at least one alcohol or in some embodiments the second composition can include greater than 60 wt % of at least one alcohol. In some embodiments the first composition can include acrylate copolymer particles, in some embodiments the second composition can include acrylate copolymer particles, or in some embodiments both the first and the second compositions can include acrylate copolymer particles. In some embodiments the second composition can be in contact with a wipe and in some embodiments both the first and the second compositions can be in contact with a wipe. In some embodiments where both the first and the second composition are in contact with a wipe, only the wipe in contact with the second composition need be a cationic coated wipe or both the wipes in contact with the first and the second composition can be a cationic coated wipe. In some such embodiments, the wipes in contact with the first and second compositions may or may not be the same type of wipe (e.g., material of the wipe).

EXAMPLES

Objects and advantages are further illustrated by the following examples, but the particular materials and amounts thereof recited in these examples, as well as other conditions and details, should not be construed to unduly limit this disclosure.

Table 1 describes the list of reagents utilized herein.

TABLE 1

| Component | Supplier | Chemical Composition |
|---|---|---|
| GPEI or G-PEI | 3M Company, St. Paul, MN | Synthesis described below |
|  | Sigma-Aldrich Corp. St. Louis, MO | Ammonium persulfate |
| BZK | Alfa Aesar, Ward Hill, MA | Benzalkonium chloride |
| BUDGE | TCI America, Portland OR | butanedioldiglycidylether |
| Butyl GPEI Solution | 3M Company, St. Paul, MN | Synthesis described below |
| Ultrez 20 | Lubrizol Advanced Material, Wickliffe, OH | carbomer |
| D/E Neutralizing Broth | Becton Dickinson, Franklin Lakes, NJ | Dey/Engley Neutralizing Broth |
| Dodecyl GPEI Solution | 3M Company, St. Paul, MN | Synthesis described below |
| 200 Proof Ethanol | Columbus Chemical Industries, Columbus, WI | Ethanol |
| 2-EHA/MMA | 3M Company, St. Paul, MN | 2-ethylhexyl acrylate (Tg −50° C.)/ methyl methacrylate (Tg 105° C.) |
| 2-EHA | Sigma-Aldrich Corp. St. Louis, MO | 2-ethylhexyl acrylate monomer |
|  | Alfa Aesar, Ward Hill, MA | $FeSO_4 \cdot H_2O$ |
| IPA | EMD Millipore, Billerica, MA | Isopropyl alcohol |
| MMA | Sigma-Aldrich Corp. St. Louis, MO | Methyl methacrylate monomer |
| HCl | J. T. Baker of Avantor Preformance Materials, Center Valley, PA | hydrochloric acid |
| Octyl GPEI Solution | 3M Company, St. Paul, MN | Synthesis described below |
| 5k PEG GPEI Solution | 3M Company, St. Paul, MN | Synthesis described below |
|  | Alfa Aesar, Haverhill MA | O-Methylisourea hemisulfate |

TABLE 1-continued

| Component | Supplier | Chemical Composition |
|---|---|---|
| PEI | Polysciences, Warrington PA | Polyethylenimine, Catalog # 00318, 70,000 MW, 30% w/w solution in water |
| Tween 20 | Sigma-Aldrich Corp. St. Louis, MO | polyoxyethylenesorbitan monolaurate |
| Tween 80 | Sigma-Aldrich Corp. St. Louis, MO | polyoxyethylenesorbitan monooleate |
| NaOH | EM Science of EMD Millipore, Billerica, MA | Sodium Hydroxide |
| | Sigma-Aldrich Corp. St. Louis, MO | Sodium metabisulfate |
| Sontara 8005 wipe | Previously available from DuPont, Wilmington, DE; currently available from Jacob Holm, Basel, Switzerland | 100% PET wipe |
| Ahlstrom 200 wipe | Previously available from Ahlstrom, Helsinki, Finland, currently available from Suominen, Helsinki, Finland | 50% PET, 50% Cellulose wipe |
| Texel 100 wipe | Texel Technical Materials, INC, Quebec, Canada | High loft 100% PET wipe |
| VITRO-SKIN® substrate | IMS Inc., Portland ME | |
| Blood agar plates | Thermo Fisher Scientific, Waltham, MA | Trypticase soy agar plates with 5% sheep's blood |

Preparation of 2-EHA/MMA Polymer

Procedure: In a 500 ml glass jar, 262.5 g of 2-EHA and 87.5 g MMA were charged. The resulting homogeneous mixture was labeled as Premix. A 3 liter, 3 neck resin flask was charged with 560 g of DI $H_2O$ and 12 g of Tween 80 surfactant. The mixture was stirred at 230 rpm at 30° C. 48 g Premix, 0.48 g ammonium persulfate, 0.12 g sodium metabisulfite and 3 g 0.15% $FeSO_4.7H_2O$ were charged to the flask followed by another 60 g DI $H_2O$. Next, 192 g of premix was metered in at 1.6 g/min over 2 hr to control the exotherm. The resulting mixture was reacted at 55° C. for about 3 hrs. The reaction was run for another 2 hrs at 70° C. The resulting latex was cooled to room temperature. The latex was filtered through 2 layers of cheese cloth (Grade 50) before use.

Preparation of Formulations

All of the formulations that were tested for their ability to remove spores from Vitro Skin were constructed in the same fashion.

First the correct amount of polymer (made as indicated above) was added to a vial, then water was added. The solution was mixed well and the pH was measured. The pH was adjusted, if necessary, with either sodium hydroxide or hydrochloric acid to a final pH around 6.5-7. Finally ethanol was added so that the solution was approximately 70% by weight ethanol, if applicable, and the solution was mixed again.

Preparation of Cationic Coated Wipes

Preparation of a 25% Guanylated Polyethyleneimine ("G-PEI") Coated Nonwoven Wipe Polyethylenimine, 70,000 MW (658.2 grams of a 30 wt. % solution in water, 4.59 amine equivalents) was charged to a 3 L 3-necked round bottom flask equipped with overhead stirring. O-methylisourea hemisulfate (141.2 grams, 1.15 equivalents) was charged to a 1 L beaker, and enough deionized water was added to bring the total weight to 652.8 grams. The contents of the beaker were stirred magnetically until all of the O-methylisourea hemisulfate dissolved, then the solution was poured into the round bottom flask. The reaction mixture was allowed to stir at ambient temperature overnight (about 22 hours).

Analysis by NMR spectroscopy indicated conversion to the desired product. Percent solids was determined using an Ohaus moisture balance (Model Number MB35, obtained from Ohaus Corp., Parsippany, N.J.), and found to be 25.3 wt. %.

A sample of the G-PEI solution prepared as above (19.79 grams of a 25.3 wt. % solids solution) was diluted to a total of 500 grams with deionized water and mixed thoroughly. In a second container BUDGE (2.35 grams) was diluted to a total of 500 grams with deionized water and mixed thoroughly. The two solutions were combined and mixed thoroughly. An appropriate amount of the solution was pipetted onto an 8" by 10" sheet of the nonwoven material The solution volume used was 20 mL for Sontara 8005 and Ahlstrom 200 or 30 mL for Texel 100 The sheet was scrunched/massaged until the solution appeared to thoroughly wet the sheet. After the sheet was thoroughly wetted it was hung to dry overnight (approximately 18 hours).

Once dry several (from 1 to 4) coated sheets were submerged in 1 L of a 50/50 mixture of methanol and water which was shaken at 150 rpm on an Orbital shaker for about 30 minutes. After the 30 minutes the wipes were removed from the solution, squeezed to remove the excess solution and submerged in 1 L of DI water, after which they were again shaken at 150 rpm for about 30 minutes. This was repeated once more with fresh DI water before the wipes were hung up to dry overnight.

After drying, small pieces of the wipe were cut off and dipped into a 0.1% solution of tartrazine dye and shaken for 5 minutes. The pieces were removed and washed three times in fresh distilled water for 5 minutes per wash. Coated pieces were stained evenly an orangish-yellow even after rinsing, unlike uncoated pieces of the wipe. This indicated the presence of a uniform, crosslinked coating of the cationic polymer on the surfaces of the nonwoven.

General Description of In-Vitro Experiment Designed to Evaluate Ability of Test Formulations to Remove Spores from Skin Like Surfaces The day before testing, 36 mm disks of VITRO-SKIN® substrates (IMS Inc., Portland, Me.) were punched out and put in a VITRO-SKIN® substrates hydration chamber containing a mixture made from 298 g of water and 52 g of glycerin (per manufacturer's instructions).

The VITRO-SKIN® substrate disks were left to hydrate for at least 24 hours before testing. On the day of testing, first 3*N+6 (N is the number of samples to be tested) 50 mL conical tubes were filled with 15 mL of D/E broth each.

Then the stainless steel plates (5" by 7.125", 24 GA) were lined up on the counter top and cleaned by first spraying with water and wiping dry with paper towels. Second the plates were sprayed with 70% IPA and wiped dry with paper towels. Once dry, two pieces of double sided tape (no longer than 2.5 cm) were placed in a cross pattern in the middle of the plates. One disk of hydrated VITRO-SKIN® substrate was placed onto the double sided tape and gently rubbed to ensure they would stick on the plates. Three pieces of VITRO-SKIN® substrates were used for each sample to be tested and three extra pieces were prepared as the recovery control.

The starting inoculum was prepped by adding 190 µl Clostridium sporogenes ATCC 3584 (~1×10$^8$ spores/ml in water) and 10 µl fetal bovine serum (FBS) to a 1.5 mL centrifuge tube and vortexing briefly to mix. The actual amount of spores and FBS added could change based on the number of samples to be tested that day, but the ratio between the two stayed constant.

Onto each piece of VITRO-SKIN® substrate 10 µl of the inoculum was placed with a pipette. The pipette tip was used to gently spread the inoculum in a circle roughly 5 mm in diameter. As a numbers control, 10 µl of the inoculum was also pipetted directly into one of the 50 mL conical tube containing 15 mL of D/E broth, this was repeated twice more. The inoculated VITRO-SKIN® substrate was left for between 30 minutes and one hour until the inoculum was visually dry.

Either before preparing the plates or during the inoculum dry time the wipes were prepared. This was done by cutting a 4" by 6" piece of the desired substrate. The cut substrate was weighed and solution in the amount of 3.5× the weight (4.5× of the weight for the Texel 100) of the substrate was added. The substrate was scrunched together to evenly distribute the solution throughout, from here on the substrate and solution combination will simply be called the wipe. The wipe was then placed into a plastic bag which was sealed to prevent it from drying out. Three wipes were prepared for each sample to be tested.

Once the inoculum had dried on the VITRO-SKIN® substrate, one piece of contaminated VITRO-SKIN® substrate was placed into one of the 50 mL conical tubes with 15 mL of D/E broth, this was repeated for a total of three pieces of VITRO-SKIN® substrates, this was the recovery control.

Figure 1B:
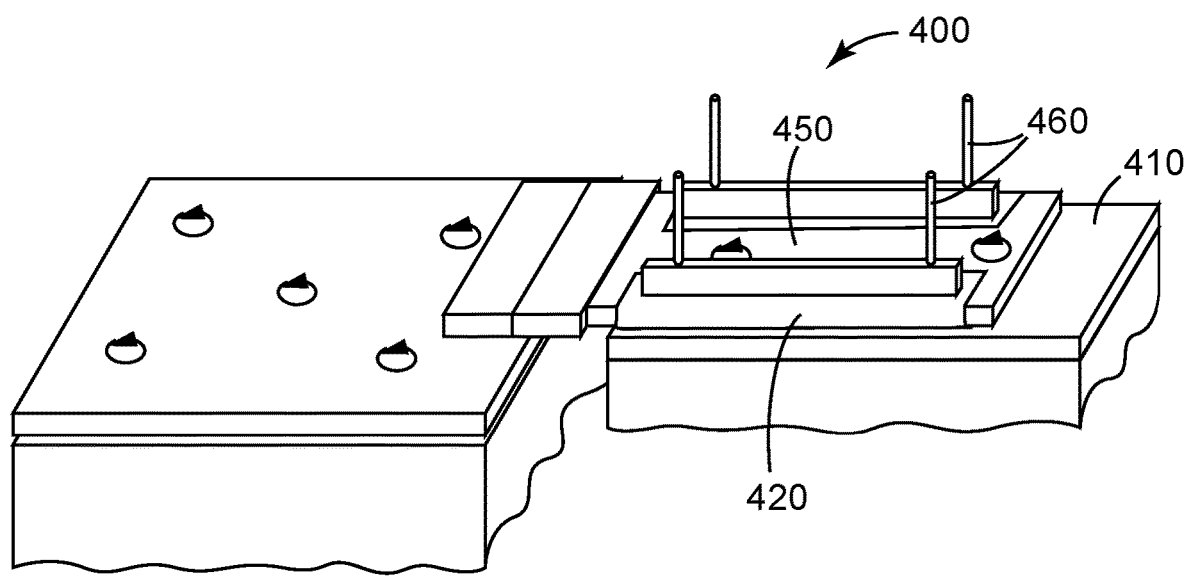

For the samples tested, a mechanical wiping device 400 was used as shown in FIGS. 1A and 1B. The wet wipe 420 was locked onto the lever arm 450 of the mechanical wiping device 400 using screw clamps 460. The lever arm 450 had a mass of about 350 g. For the two-step method, approximately 0.5 mL of the first solution was placed onto the center of the inoculated VITROSKIN® substrate attached to a stainless steel plate located on platform 410. For the one step method no solution was added to the inoculated VITROSKIN® substrate. Then the lever arm 450 with wet wipe 420 attached was lowered onto one of the contaminated plates (not shown) on platform 410 so that the inoculated VITRO-SKIN® substrate was in the center of the wipe. The mechanical wiping device 400 was switched on, with the lever arm 450 operating at a rotational speed of about 100 rpm to wipe the surface of contaminated plate for 15 seconds. After wiping the wet wipe 420 was then removed from the "wiped plate" and the VITRO-SKIN® substrate was removed and placed in a 50 mL conical tube with 15 mL of D/E. For each wipe example, this step was repeated to give n=3 wiped VITRO-SKIN® substrates.

After all the samples were collected all of the 50 mL conical tubes were sonicated for one minute then vortexed for one minute. A one milliliter aliquot was removed and added to a 1.5 mL centrifuge tube. This was done twice for each sample. The tube was then heated to 80 degrees C. for ten minutes. After cooling for three minutes 0.25 mL was removed from one tube for each sample and plated directly onto blood agar plates, for the other tube each sample was serially diluted in Butterfields Buffer from $10^{-1}$ to $10^{-4}$, then 1 mL of each of the serial dilutions was plated onto 3M PETRIFILM® AC plates. Both blood agar plates and 3M PETRIFILM® AC plates were incubated in an anaerobic chamber at 37 degrees C. for approximately 20 hours. After incubation the plates were removed, counted and log reduction values were calculated.

Working Standard

In the examples that follow, a "Working Standard" is indicated within various examples. Because the nature of the testing utilized herein, results may seem to vary from day to day, from testing personnel to testing personnel, or both. Within the different sets of examples, a single one that is the same is indicated as a Working Standard where applicable. This affords a more meaningful comparison of spore removal across examples.

Comparative Example 1

Sontara 8005 wipes were coated (or not) with GPEI, dodecyl GPEI or butyl GPEI as discussed above. 2-EHA/MMA polymer was synthesized as discussed above and the compositions for Comparative 1a to 1d were prepared as discussed above. The ability of the compositions to remove spores was tested as discussed above using a one-step method on VITRO-SKIN® substrate.

| Example 1 | Comparative 1a | Comparative 1b | Comparative 1c | Comparative 1d |
|---|---|---|---|---|
| 2-EHA/MMA polymer | 4 | 4 | 4 | 4 |
| Ethanol | 70 | 70 | 70 | 70 |
| Wipe | Sontara 8005 | Sontara 8005 | Sontara 8005 | Sontara 8005 |
| Water | 26 | 26 | 26 | 26 |
| Coated? | No | Yes | Yes | Yes |
| Coating Type | N/A | GPEI | dodecyl GPEI | Butyl GPEI |
| Log Reduction | 1.80 | 1.65 | 1.39 | 1.52 |
| Standard Deviation | 0.23 | 0.05 | 0.16 | 0.22 |

These comparative examples show that when an acrylate copolymer particle containing composition in 70 wt % ethanol is used in either a coated wipe or an uncoated wipe, there is very little difference in spore removal, and depending on the type of coating, there may be a small decrease in spore removal.

Comparative Example 2

2-EHA/MMA polymer was synthesized as discussed above and the compositions for Comparative Examples 2a to 2d were prepared as discussed above. The ability of the compositions to remove spores was tested as discussed above using a two-step method with uncoated Texel 100 wipes on VITRO-SKIN® substrate.

| Comparative Example 2 | Comparative 2a | Comparative 2b | Comparative 2c | Comparative 2d |
|---|---|---|---|---|
| First Step - Solution added onto VITRO-SKIN ® substrates | | | | |
| 2-EHA/MMA polymer | No solution on VITRO-SKIN ® substrate | 4 | 4 | 4 |
| Ethanol | | 70 | 70 | 0 |
| Water | | 26 | 26 | 96 |
| Second Step - VITRO-SKIN ® substrates wiped with pre-wetted wipes as indicated below | | | | |
| Wipe | Texel 100 | Texel 100 | Texel 100 | Texel 100 |
| Coated? | No | No | No | No |
| Coating Type | N/A | N/A | N/A | N/A |
| Ethanol | 70 | 70 | 0 | 70 |
| Tween 20 | 0 | 0 | 0.1 | 0 |
| Water | 30 | 30 | 99.9 | 30 |
| Log Reduction | 0.83 | 0.48 | 1.70 | 1.75 |
| Standard Deviation | 0.14 | 0.04 | 0.10 | 0.06 |

As seen from Comparative Example 2a, a 70% ethanol wipe by itself gives less than 1 log of spore removal. When a first composition containing acrylate copolymer particles and 70 wt % alcohol and a wipe loading solution also containing 70 wt % alcohol is included, spore removal decreased to just under 0.5 logs (Comparative Example 2b). However if water is used in either the wipe loading solution or the first solution, spore removal increases greatly to approximately 1.7 logs.

Example 3

2-EHA/MMA polymer was synthesized as discussed above and the compositions for Comparative Example 3a and 3c and Example 3b were prepared as discussed above. The ability of the compositions to remove spores was tested as discussed above using a two-step method with GPEI coated Sontara 8005 wipes on VITRO-SKIN® substrate.

| Example 3 | Comparative 3a | Example 3b* | Comparative 3c |
|---|---|---|---|
| First Step - Solution added onto VITRO-SKIN ® substrates | | | |
| 2-EHA/MMA polymer | 0 | 4 | 0 |
| Ethanol | 0 | 70 | 70 |
| Water | 100 | 26 | 30 |
| Second Step - VITRO-SKIN ® substrates wiped with pre-wetted wipe | | | |
| Wipe | Sontara 8005 | Sontara 8005 | Sontara 8005 |
| Coated? | Yes | Yes | Yes |
| Coating Type | GPEI | GPEI | GPEI |
| Tween 20 | 0.1 | 0.1 | 0.1 |
| Water | 99.9 | 99.9 | 99.9 |
| Log Reduction | 2.24 | 3.68 | 2.72 |
| Standard Deviation | 0.09 | 0.21 | 0.25 |

*Working Standard

An uncoated wipe with just water has 1.7 logs of spore removal (Comparative 2c). If 0.5 mL of water is placed on the VITRO-SKIN® substrate and wiped away with a coated wipe loaded only with water, removal increased to 2.2 logs (Comparative 3a). Surprisingly, when 0.5 mL of 70% ethanol is wiped away with a coated water wipe removal is 2.7 logs (Comparative 3c) and when 0.5 mL of a composition containing acrylate copolymer particles and ethanol is wiped away by a coated water wipe there is nearly 3.7 logs of spore removal (Example 3b).

It is noted that Example 3b is indicated as a working standard.

Example 4

2-EHA/MMA polymer was synthesized as discussed above and the compositions for Examples 4a to 4d were prepared as discussed above. The ability of the compositions to remove spores was tested as discussed above using a two-step method with GPEI, 5K PEG GPEI, Octyl GPEI and PEI coated Sontara 8005 wipes on VITRO-SKIN® substrate.

| Example 4 | Example 4a* | Example 4b | Example 4c | Example 4d |
|---|---|---|---|---|
| First Step - Solution added onto VITRO-SKIN ® substrates | | | | |
| 2-EHA/MMA polymer | 4 | 4 | 4 | 4 |
| Ethanol | 70 | 70 | 70 | 70 |
| Water | 26 | 26 | 26 | 26 |
| Second Step - VITRO-SKIN ® substrates wiped with pre-wetted wipe | | | | |
| Wipe | Sontara 8005 | Sontara 8005 | Sontara 8005 | Sontara 8005 |
| Coated? | Yes | Yes | Yes | Yes |
| Coating Type | GPEI | 5K PEG GPEI | Octyl GPEI | PEI |
| Tween 20 | 0.1 | 0.1 | 0.1 | 0.1 |
| Water | 99.9 | 99.9 | 99.9 | 99.9 |
| Log Reduction | 2.74 | 2.66 | 2.76 | 2.64 |
| Standard Deviation | 0.12 | 0.14 | 0.07 | 0.12 |

*Working Standard

The data shows that there is no difference in spore removal when utilizing various different cationic coatings.

Example 5

2-EHA/MMA polymer was synthesized as discussed above and the compositions for Examples 5a to 5d and Comparative 5e were prepared as discussed above. The ability of the compositions to remove spores was tested as discussed above using a two-step method with GPEI coated Sontara 8005 wipes on VITRO-SKIN® substrate.

| Example 5 | Example 5a* | Example 5b | Example 5c | Example 5d | Comparative 5e |
|---|---|---|---|---|---|
| First Step - Solution added onto VITRO-SKIN ® substrates | | | | | |
| 2-EHA/MMA polymer | 4 | 4 | 4 | 4 | 4 |
| Ethanol | 70 | 0 | 0 | 0 | 0 |
| Water | 26 | 96 | 96 | 96 | 96 |
| Second Step - VITRO-SKIN ® substrates wiped with pre-wetted wipe | | | | | |
| Wipe | Sontara 8005 | Sontara 8005 | Sontara 8005 | Sontara 8005 | Sontara 8005 |
| Coated? | Yes | Yes | Yes | Yes | No |
| Coating Type | GPEI | GPEI | GPEI | GPEI | N/A |
| Ethanol | 0 | 70 | 70 | 90 | 70 |
| Tween 20 | 0.1 | 0 | 0 | 0 | 0 |
| BZK | 0 | 0 | 0.1 | 0 | 0 |
| Water | 99.9 | 30 | 29.9 | 10 | 30 |
| Log Reduction | 2.22 | 2.92 | 2.44 | 2.70 | 1.96 |
| Standard Deviation | 0.07 | 0.12 | 0.22 | 0.24 | 0.05 |

*Working Standard

Example 6

2-EHA/MMA polymer was synthesized as discussed above and the compositions for Examples 6a and Comparative 6b were prepared as discussed above. The ability of the compositions to remove spores was tested as discussed above using a two-step method with GPEI coated Sontara 8005 wipes on VITRO-SKIN® substrate.

| Example 6 | Example 6a* | Comparative 6b |
|---|---|---|
| First Step - Solution added onto VITRO-SKIN® substrates | | |
| 2-EHA/MMA polymer | 4 | 0 |
| Ethanol | 70 | 70 |
| Water | 26 | 30 |
| Second Step - VITRO-SKIN® substrates wiped with pre-wetted wipe | | |
| Wipe | Sontara 8005 | Sontara 8005 |
| Coated? | Yes | Yes |
| Coating Type | GPEI | GPEI |
| Tween 20 | 0.1 | 0.1 |
| Water | 99.9 | 99.9 |
| Log Reduction | 2.93 | 2.63 |
| Standard Deviation | 0.03 | 0.24 |

*Working Standard

Example 7

2-EHA/MMA polymer was synthesized as discussed above and the compositions for Examples 7b and Comparative 7a were prepared as discussed above. The ability of the compositions to remove spores was tested as discussed above using a two-step method with GPEI coated Sontara 8005 wipes on VITRO-SKIN® substrate.

| Example 7 | Comparative 7a | Example 7b* |
|---|---|---|
| First Step - Solution added onto VITRO-SKIN® substrates | | |
| 2-EHA/MMA polymer | 0 | 4 |
| Ethanol | 70 | 70 |
| Water | 30 | 26 |
| Second Step - VITRO-SKIN® substrates wiped with pre-wetted wipe | | |
| Wipe | Sontara 8005 | Sontara 8005 |
| Coated? | Yes | Yes |
| Coating Type | GPEI | GPEI |
| Tween 20 | 0.1 | 0.1 |
| Water | 99.9 | 99.9 |
| Log Reduction | 2.45 | 3.46 |
| Standard Deviation | 0.12 | 0.22 |

*Working Standard

Example 6a was repeated on a separate day as Example 7b and both are presented herein. On both days, the Comparative Examples had a lower log reduction than the Examples. See the explanation of the Working Standard above.

Example 8

2-EHA/MMA polymer was synthesized as discussed above and the compositions for Examples 8a, 8b and Comparative 8c were prepared as discussed above. The ability of the compositions to remove spores was tested as discussed above using a two-step method with GPEI coated (and non-coated) wipes (Sontara 8005, Ahlstrom 200) on VITRO-SKIN® substrate.

| Example 8 | Example 8a* | Example 8b | Comparative 8c |
|---|---|---|---|
| First Step - Solution added onto VITRO-SKIN® substrates | | | |
| 2-EHA/MMA polymer | 4 | 4 | 4 |
| Ethanol | 70 | 70 | 70 |
| Water | 26 | 26 | 26 |
| Second Step - VITRO-SKIN® substrates wiped with pre-wetted wipe | | | |
| Wipe | Sontara 8005 | Ahlstrom 200 | Sontara 8005 |
| Coated? | Yes | Yes | No |
| Coating Type | GPEI | GPEI | N/A |
| Tween 20 | 0.1 | 0.1 | 0.1 |
| Water | 99.9 | 99.9 | 99.9 |
| Log Reduction | 2.38 | 2.86 | 2.03 |
| Standard Deviation | 0.09 | 0.24 | 0.05 |

*Working Standard

Thus, embodiments of methods of removing spores are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

Exemplary Embodiments

1. A method comprising:
   contacting a skin surface with a first liquid composition; and
   then contacting the skin surface with a cationic coated article loaded with a second liquid composition, while at least some portion of the first liquid composition remains on the skin surface,
   wherein one or both of the first liquid composition or the second liquid composition comprises acrylate copolymer particles dispersed therein, the acrylate copolymer particles comprising the reaction product of a reaction mixture, the reaction mixture comprising monomers, the monomers comprising:
   from about 5 wt % to about 50 wt % of at least one high Tg monomer where the wt % of the high Tg monomer is with respect to the total weight of the monomers in the reaction mixture; and
   from about 20 wt % to about 80 wt % of at least one low Tg monomer where the wt % of the low Tg monomer is with respect to the total weight of the monomers in the reaction mixture,
   wherein the particles have a number average diameter of at least about 100 nm,
   wherein at least one and only one of the first or the second composition comprises greater than or equal to 60 wt % of at least one alcohol.

2. The method according to embodiment 1, wherein the step of contacting a first composition with the skin surface is accomplished via contacting the skin surface with only the first composition.

3. The method according to any of embodiments 1 or 2, wherein the step of contacting the surface with the first composition comprises applying the composition to the skin surface.

4. The method according to embodiment 3, wherein the step of applying the composition to the skin surface comprises spraying, dispensing, dipping, pouring, or some combination thereof on to the skin surface.

5. The method according to any of embodiments 1 to 4 further comprising subjecting the skin surface in contact with the first composition to mechanical action before contacting the skin surface to the cationic coated article loaded with a second composition.

6. The method according to embodiment 5, wherein the mechanical action lasts at least about 5 seconds.

7. The method according to embodiment 5, wherein the step of subjecting the skin surface in contact with the first composition to mechanical action comprises rubbing the skin surface, moving an article across the skin surface, or some combination thereof.

8. The method according to any of embodiments 1 to 7, wherein the first composition comprises greater than or equal to 60 wt % alcohol.

9. The method according to embodiment 8, wherein there is at least about 65 wt % of at least one alcohol in the first composition based on the total weight of the first composition.

10. The method according to embodiment 8, wherein there is at least about 70 wt % of at least one alcohol in the first composition based on the total weight of the first composition.

11. The method according to embodiment 8, wherein there is not greater than 95 wt % of at least one alcohol in the first composition based on the total weight of the first composition.

12. The method according to any of embodiments 1 to 7, wherein the second composition comprises greater than or equal to 60 wt % alcohol.

13. The method according to embodiment 12, wherein there is at least about 65 wt % of at least one alcohol in the second composition based on the total weight of the second composition.

14. The method according to embodiment 12, wherein there is at least about 70 wt % of at least one alcohol in the second composition based on the total weight of the second composition.

15. The method according to embodiment 12, wherein there is not greater than 85 wt % of at least one alcohol in the second composition based on the total weight of the second composition.

16. The method according to any of embodiments 1 to 15, wherein there is more of the at least one low Tg monomer than there is of the at least one high Tg monomer by weight in the reaction mixture that forms the first composition.

17. The method according to any of embodiments 1 to 15, wherein there is not greater than about 5 wt % of the acrylate copolymer particles in the first composition based on the total weight of the first composition.

18. The method according to any of embodiments 1 to 15, wherein there is from about 0.5 wt % to about 4 wt % of the acrylate copolymer particles in the first composition based on the total weight of the first composition.

19. The method according to any of embodiments 1 to 15, wherein there is more of the at least one low Tg monomer than there is of the at least one high Tg monomer by weight in the reaction mixture that forms the second composition.

20. The method according to any of embodiments 1 to 15, wherein there is not greater than about 5 wt % of the acrylate copolymer particles in the second composition based on the total weight of the second composition.

21. The method according to any of embodiments 1 to 15, wherein there is from about 0.5 wt % to about 4 wt % of the acrylate copolymer particles in the second composition based on the total weight of the second composition.

22. The method according to any of embodiments 1 to 21, wherein the acrylate copolymer is the reaction product of about 20 wt % to about 40 wt % of the at least one high Tg monomer based on the total weight of the monomers in the reaction mixture.

23. The method according to any one of embodiments 1 to 22, wherein the acrylate copolymer is the reaction product of about 60 wt % to about 80 wt % of the at least one low Tg monomer based on the total weight of the monomers in the reaction mixture.

24. The method according to any of embodiments 1 to 23, wherein the at least one low Tg monomer has an alkyl carbon chain length from about 4 to about 10.

25. The method according to any of embodiments 1 to 24, wherein the at least one low Tg monomer has a Tg from about −20° C. to about −60° C.

26. The method according to any of embodiments 1 to 25, wherein the at least one high Tg monomer has a carbon chain length from about 1 to about 3.

27. The method according to any of embodiments 1 to 26, wherein the at least one high Tg monomer has a Tg from about 40° C. to about 150° C.

28. The method according to any of embodiments 1 to 27, wherein the acrylate copolymer particles have a number average diameter from about 200 to about 500 nm.

29. The method according to any of embodiments 1 to 28, wherein the cationic coated article comprises a cationic coated wipe.

30. The method according to any of embodiments 1 to 29, wherein the cationic coated article comprises a guanidinyl-containing polymer.

31. The method according to embodiment 30, wherein the guanidinyl-containing polymer is a reaction product of (a) a guanylating agent and (b) a carbonyl-containing polymer precursor or an amino-containing polymer precursor.

32. The method according to embodiment 30, wherein the guanidinyl-containing polymer is of the Formula (I):

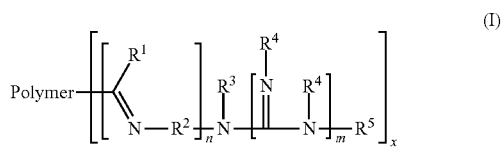

wherein:
$R^1$ is hydrogen, $C_1$-$C_{12}$(hetero)alkyl, a $C_5$-$C_{12}$ (hetero)aryl, or a residue of the polymer chain;
$R^2$ is a covalent bond, a $C_2$ to $C_{12}$ (hetero)alkylene, or a $C_5$-$C_{12}$ (hetero)arylene;
$R^3$ is hydrogen, $C_1$-$C_{12}$ (hetero)alkyl, $C_5$-$C_{12}$ (hetero)aryl, or a residue of the polymer chain when n is 0;
each $R^4$ is independently hydrogen, $C_1$-$C_{12}$ (hetero)alkyl, $C_5$-$C_{12}$ (hetero)aryl;
$R^5$ is hydrogen, $C_1$-$C_{12}$ (hetero)alkyl, or $C_5$-$C_{12}$ (hetero)aryl, or —$N(R^4)_2$;
n is 0 or 1;
m is 1 or 2; and
x is an integer equal to at least 1.

33. The method according to embodiment 32, wherein the guanidinyl-containing polymer is of Formula (II):

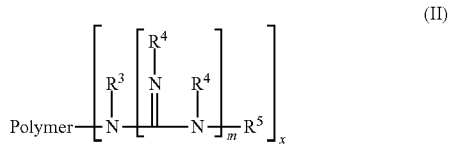

34. The method according to embodiment 32, wherein the guanidinyl-containing polymer is of Formula (IV):

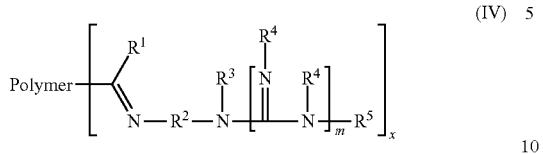

35. The method according to any one of embodiments 30 to 32 or 34, wherein the guanidinyl-containing polymer is a reaction product of (a) a guanylating agent and (b) a carbonyl-containing polymer precursor, and wherein 1 to 90 mole percent of the carbonyl groups of the carbonyl-containing polymer precursor are reacted with the guanylating agent.

36. The method according to any one of embodiments 30 to 32 or 34, wherein the guanidinyl-containing polymer is a reaction product of (a) a guanylating agent and (b) a carbonyl-containing polymer precursor, and wherein the guanidinyl-containing polymer is crosslinked with a N,N'-(hetero)alkylenebis(meth)acrylamide.

37. The method according to any one of embodiments 30 to 33, wherein the guanidinyl containing polymer is a reaction product of a (a) guanylating agent and (b) an amino-containing polymer precursor, and wherein 1 to 90 mole percent of the amino groups of the amino-containing polymer precursor are reacted with the guanylating agent.

38. The method according to any one of embodiments 30 to 33, wherein the guanidinyl-containing polymer is a reaction product of (a) a guanylating agent and (b) an amino-containing polymer, and wherein the guanidinyl-containing polymer is crosslinked with a polyglycidylether.

39. The wipe according to any one of embodiments 30 to 38, wherein guanidinyl-containing polymer is present in an amount of 0.1 weight percent to 10 weight percent based on a total weight of the wipe.

40. The method according to any of embodiments 1 to 39, wherein the at least one alcohol is selected from ethanol, n-propanol, 2-propanol or mixtures thereof.

41. The method according to any of embodiments 1 to 40, wherein the first composition, the second composition or both further comprises an antimicrobial agent in addition to the at least one alcohol.

42. The method according to embodiment 41, wherein the antimicrobial agent is cationic.

43. The method according to embodiment 1, wherein the step of contacting a first composition with the skin surface is accomplished via contacting the skin surface with the first composition in contact with a second article.

44. The method according to embodiment 43, wherein the second article is a wipe.

45. The method according to embodiment 44, wherein the second article is a cationic coated wipe.

46. The method according to any of embodiments 1 to 45, wherein the first composition comprises acrylate copolymer particles dispersed therein.

47. The method according to any of embodiments 1 to 46, wherein the second composition comprises acrylate copolymer particles dispersed therein.

The invention claimed is:

1. A method comprising:
contacting a surface with a first liquid composition;
then contacting the surface with a cationic coated article loaded with a second liquid composition, while at least some portion of the first liquid composition remains on the surface, and
removing spores from the surface;
wherein one or both of the first liquid composition or the second liquid composition comprises acrylate copolymer particles dispersed therein, wherein the acrylate copolymer particles are present in one or both of the first liquid composition or the second liquid composition in amount of not greater than 5 wt %, the acrylate copolymer particles comprising the reaction product of a reaction mixture, the reaction mixture comprising monomers, the monomers comprising:
from about 5 wt % to about 50 wt % of at least one high Tg monomer having a Tg of not less than 40° C. where the wt % of the high Tg monomer is with respect to the total weight of the monomers in the reaction mixture; and
from about 20 wt % to about 80 wt % of at least one low Tg monomer having a Tg of not greater than −30° C. where the wt % of the low Tg monomer is with respect to the total weight of the monomers in the reaction mixture,
wherein the acrylate copolymer particles are of a formula:

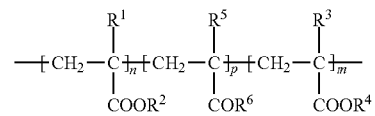

where $R^1$ is H or —$CH_3$, $R^2$ is H, —$CH_3$ or —$CH_2CH_3$, $R^3$ is H or —$CH_3$, $R^4$ is —$CH_2(CH_2)_xCH_3$ where x is an integer from one (1) to eight (8) and the alkyl chain can be straight or branched, $R^5$ is H or —$CH_3$, $R^6$ is OH, $NH_2$, $NHCH_3$, $N(CH_3)_2$, —$OCH_2CH_2OH$, m is an integer from 20 to 1,500,000, n is an integer from 20 to 1,500,000, p is an integer from zero (0) to 1,500,000, with the proviso that m is greater than n, and both m and n are greater than p;
wherein the acrylate copolymer particles have a number average diameter of at least about 100 nm, and wherein;
A) either liquid composition may contain at least one alcohol, however at least one, and only one of the compositions will have at least one alcohol present in an amount greater than or equal to 60 wt % of the composition; and
B) the first liquid composition must contain at least one of (i) greater than or equal to 60 wt % of at least one alcohol, or (ii) the acrylate copolymer particles dispersed therein.

2. The method according to claim 1, wherein the surface is skin.

3. The method according to claim 1, wherein the step of contacting the surface with the first composition comprises applying the composition to the surface.

4. The method according to claim 3, wherein the step of applying the composition to the surface comprises spraying, dispensing, dipping, pouring, or some combination thereof on to the surface.

5. The method according to claim 1 further comprising subjecting the surface in contact with the first composition to mechanical action before contacting the surface to the cationic coated article loaded with a second composition.

6. The method according to claim 1, wherein the first composition comprises greater than or equal to 60 wt % alcohol.

7. The method according to claim 1, wherein the second composition comprises greater than or equal to 60 wt % alcohol.

8. The method according to claim 1, wherein there is not greater than about 5 wt % of the acrylate copolymer particles in the first composition based on the total weight of the first composition.

9. The method according to claim 1, wherein there is not greater than about 5 wt % of the acrylate copolymer particles in the second composition based on the total weight of the second composition.

10. The method according to claim 1, wherein the cationic coated article comprises a guanidinyl-containing polymer.

11. The method according to claim 10, wherein the guanidinyl-containing polymer is a reaction product of (a) a guanylating agent and (b) a carbonyl-containing polymer precursor or an amino-containing polymer precursor.

12. The method according to claim 10, wherein the guanidinyl-containing polymer is of the Formula (I):

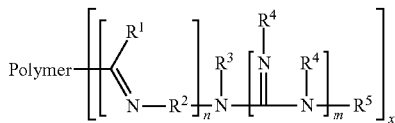

wherein:
$R^1$ is hydrogen, $C_1$-$C_{12}$(hetero)alkyl, a $C_5$-$C_{12}$ (hetero)aryl, or a residue of the polymer chain;

$R^2$ is a covalent bond, a $C_2$ to $C_{12}$ (hetero)alkylene, or a $C_5$-$C_{12}$ (hetero)arylene;

$R^3$ is hydrogen, $C_1$-$C_{12}$ (hetero)alkyl, $C_5$-$C_{12}$ (hetero)aryl, or a residue of the polymer chain when n is 0;

each $R^4$ is independently hydrogen, $C_1$-$C_{12}$ (hetero)alkyl, $C_5$-$C_{12}$ (hetero)aryl;

$R^5$ is hydrogen, $C_1$-$C_{12}$ (hetero)alkyl, or $C_5$-$C_{12}$ (hetero)aryl, or —N$(R^4)_2$;

n is 0 or 1;
m is 1 or 2; and
x is an integer equal to at least 1.

13. The method according to claim 10, wherein the guanidinyl-containing polymer is of Formula (II):

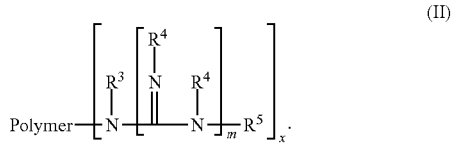

14. The method according to claim 10, wherein the guanidinyl-containing polymer is of Formula (IV):

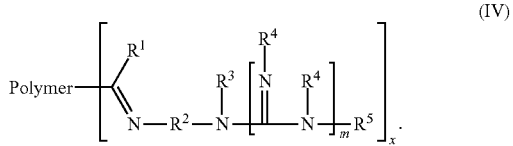

15. The method according to claim 1, wherein the step of contacting a first composition with the surface is accomplished via contacting the surface with the first composition in contact with a wipe.

* * * * *